United States Patent
Rotem-Yehudar et al.

(10) Patent No.: US 9,580,504 B1
(45) Date of Patent: Feb. 28, 2017

(54) PIDILIZUMAB MONOCLONAL ANTIBODY THERAPY FOLLOWING STEM CELL TRANSPLANTATION

(71) Applicant: CureTech Ltd., Yavne (IL)

(72) Inventors: Rinat Rotem-Yehudar, Tel Aviv (IL); Michael Schickler, Mazkeret Batya (IL)

(73) Assignee: CureTech Ltd., Yavne (IL)

( * ) Notice: Subject to any disclaimer, the term of this patent is extended or adjusted under 35 U.S.C. 154(b) by 0 days.

(21) Appl. No.: 14/536,343

(22) Filed: Nov. 7, 2014

Related U.S. Application Data

(60) Provisional application No. 61/901,015, filed on Nov. 7, 2013.

(51) Int. Cl.
  *C07K 16/28* (2006.01)
  *A61K 39/395* (2006.01)

(52) U.S. Cl.
  CPC ...... *C07K 16/2803* (2013.01); *C07K 16/2887* (2013.01); *C07K 16/2896* (2013.01); *C07K 2317/24* (2013.01); *C07K 2317/31* (2013.01); *C07K 2317/565* (2013.01)

(58) Field of Classification Search
  None
  See application file for complete search history.

(56) References Cited

U.S. PATENT DOCUMENTS

| | | | |
|---|---|---|---|
| 5,001,225 A * | 3/1991 | Taylor | A61K 47/48507 424/131.1 |
| 5,225,539 A | 7/1993 | Winter | |
| 5,530,101 A | 6/1996 | Queen | |
| 5,585,089 A | 12/1996 | Queen | |
| 5,618,920 A | 4/1997 | Robinson | |
| 5,658,741 A | 8/1997 | Bolton | |
| 5,897,862 A | 4/1999 | Hardy | |
| 6,074,635 A | 6/2000 | Abrignani | |
| 6,294,654 B1 | 9/2001 | Bogen | |
| 7,332,582 B2 | 2/2008 | Hardy | |
| 7,524,498 B2 | 4/2009 | Hardy | |
| 7,638,326 B2 | 12/2009 | June | |
| 7,695,715 B2 | 4/2010 | Hardy | |
| 7,981,416 B2 | 7/2011 | Hardy | |
| 8,686,119 B2 | 4/2014 | Rotem-Yehudar | |
| 8,747,847 B2 | 6/2014 | Rotem-Yehudar | |
| 2003/0017153 A1 | 1/2003 | Boyd | |
| 2003/0026800 A1 | 2/2003 | Hardy | |
| 2004/0175827 A1 | 9/2004 | Fowler et al. | |
| 2005/0025758 A1 | 2/2005 | Harrison et al. | |
| 2006/0084055 A1 | 4/2006 | Gaiger et al. | |
| 2007/0172847 A1 * | 7/2007 | Bonavida | G01N 33/57426 435/6.14 |
| 2009/0123413 A1 | 5/2009 | Hardy et al. | |
| 2010/0092436 A1 | 4/2010 | Bonyhadi et al. | |
| 2011/0117085 A1 * | 5/2011 | Rotem-Yehudar | A61K 39/39558 424/133.1 |

FOREIGN PATENT DOCUMENTS

| | | |
|---|---|---|
| WO | 91/09967 | 7/1991 |
| WO | 00/58363 | 10/2000 |
| WO | 03/033644 | 4/2003 |
| WO | 03/099196 | 12/2003 |

OTHER PUBLICATIONS

Lymphoma Research Foundation (Hodgkin Lymphoma, http://www.lymphoma.org/site/pp.asp?c=bkLTKaOQLmK8E&b=6300137, 2012).*
Aksentijevich et al., (2006) Clinical outcome following autologous and allogeneic blood and marrow transplantation for relapsed diffuse large-cell non-Hodgkin's lymphoma. Biol Blood Marrow Transplant 12(9): 965-72.
Alousi et al., (2008) Disease staging with positron emission tomography or gallium scanning and use of rituximab predict outcome for patients with diffuse large B-cell lymphoma treated with autologous stem cell transplantation. Br J Haematol 142(5): 786-92.
Armand et al., (2013) Disabling immune tolerance by programmed death-1 blockade with pidilizumab after autologous hematopoietic stem-cell transplantation for diffuse large B-cell lymphoma: results of an international phase II trial. J Clin Oncol 31(33): 4199-206.
Armand et al., (2013) Prognostic factors for patients with diffuse large B cell lymphoma and transformed indolent lymphoma undergoing autologous stem cell transplantation in the positron emission tomography era. Br J Haematol 160(5): 608-17.
Becherer et al., (2002) Positron emission tomography with [18F]2-fluoro-D-2-deoxyglucose (FDG-PET) predicts relapse of malignant lymphoma after high-dose therapy with stem cell transplantation. Leukemia 16(2): 260-7.
Bendig (1995) Humanization of Rodent Monoclonal Antibodies by CDR Gafting Methods: A companion to methods in enzymology 8: 83-93.
Bresalier et al., (1991) Mucin production by human colonic carcinoma cells correlates with their metastatic potential in animal models of colon cancer metastasis. J Clin Invest 87(3): 1037-1045.
Bruccoleri and Karplus (1987) Predicton of the folding of short polypeptide segments by uniform conformational sampling. Biopolymers 26(1): 137-168.
Carter et al., (1992) High level *Escherichia coli* expression and production of a bivalent humanized antibody fragment. Biotechnology (N Y) 10(2): 163-167.
Casset et al., (2003) a peptide mimetic of an anti-CD4 monoclonal antibody by rational design. Biochem Biophys Res Commun 307(1): 198-205.
Cheson et al., (2007) Revised response criteria for malignant lymphoma. J Clin Oncol 25(5): 579-86.
Chotia and Lesk (1987) Canonical structures for the hypervariable regions of immunoglobulins. J Mol Biol 196(4): 901-917.
Chotia et al., (1989) Conformations of immunoglobulin hypervariable regions. Nature 342(6252): 877-883.

(Continued)

*Primary Examiner* — Peter J Reddig
(74) *Attorney, Agent, or Firm* — Winston & Strawn LLP

(57) ABSTRACT

Methods for treating specific populations of cancer patients, specifically patients suffering from cancer who undergo stem cell transplantation and were classified as positive by a pre-transplant metabolic imaging, by administering to the subject a therapeutically effective amount of a pidilizumab monoclonal antibody.

23 Claims, 8 Drawing Sheets

(56) References Cited

OTHER PUBLICATIONS

Chotia et al., (1992) Structural repertoire of the human VH segments. J Mol Biol 227(3): 799-817.
Clark (2000) Antibody humanization: a case of the 'Emperors's new clothes'? Immunol Today 21(8): 397-402.
Coiffier (2001) Positron emission tomography and gallium metabolic imaging in lymphoma. Curr Oncol Rep 3(3): 266-70.
Colman (1994) Effects of amino acid sequence changes on antibody-antigen interactions. Res Immunol 145(1): 33-36.
Cremerius et al., (2002) Pre-transplant positron emission tomography (PET) using fluorine-18-fluoro-deoxyglucose (FDG) predicts outcome in patients treated with high-dose chemotherapy and autologous stem cell transplantation for non-Hodgkin's lymphoma. Bone Marrow Transplant 30(2): 103-11.
Di Giacomo et al., (2010) The emerging toxicity profiles of anti-CTLA-4 antibodies across clinical indications. Semin Oncol 37(5): 499-507.
Dickinson et al., 2010)Impoved survival for ralapsed diffuse large B cell lymphoma is predicted by a negative pre-transplant FDG-PET scan following salvage chemotherapy. Br J Haematol 150(1): 39-45.
Fang et al., (1994) Human rheumatoid factors with restrictive specificity for rabbit immunoglobulin G: auto- and multi-reactivity, diverse VH gene segment usage and preferential usage of V lambda lllb. J Exp Med 179(5): 1445-56.
Foote and Winter (1992) Antibody famework esidues affecting the conformation of the hyperarable loops J Mol Biol 224(2): 487-499.
Friedberg (2011) Relapsed/refractory diffuse large B-cell lymphoma. Hematology Am Soc Hematol Educ Program 2011: 498-505.
Gisselbrecht et al., (2010) Salvage regimens with autologous transplantation for relapsed large B-cell lymphoma in the rituximab era. J Clin Oncol 28(27): 4184-90.
Habu et al., (1979) Surface markers on natural killer cells of the mouse. Eur J Immunol 9(12): 938-42.
Hardy et al., (1989) A monoclonal antibody to human B lymphoblastoid cells activates human and murine T lymphocytes. Cell Immunol 118(1): 22-29.
Hardy et al., (1994) A monoclonal antibody against a human B lymphoblastoid cell line induces tumor regression in mice. Cancer Res 54(22): 5793-5796.
Hardy et al., (1995) Activation of human lymphocytes by a monoclonal antibody to B lymphoblastoid cells; molecular mass and distribution of binding protein. Cancer Immunology, Immunotherapy 40(6): 376-382.
Hardy et al., (1997) A lymphocyte-activating monoclonal antibody induces regression of human tumors in severe combined immunodeficient mice. Proc Natl Acad Sci U S A 94(11): 5756-60.
Hardy et al (1997) Immune stimulatory and anti-tumor properties of anti-CD3 and BAT monoclonal antibodies: a comparative study. Hum Antibodies 8(2): 95-8.
Hardy et al., (2001) Treatment with BAT monoclonal antibody decreases tumor burden in a murine model of leukemia/lymphoma. Int J Oncol 19(5): 897-902.
Hardy et al., (2005) BAT mAb induces lymphopoiesis in nude mice. Int Immunol 17(5): 615-619.
Hardy et al., (2005) BAT monoclonal antibody immunotherapy of human metastatic colorectal carcinoma in mice. Cancer Lett 229(2): 217-22.
Hardy et al., (2005) Cancer disease predictive diagnosis: BAT/CD3-positive lymphocytes in cancer patients. Int J Oncol 26(4): 971-5.
Hunt et al., (2000) Orthotopic human lung carcinoma xenografts in BALB/c mice immunosuppressed with anti-CD4 monoclonal antibodies and chronic alcohol consumption. Cancer 88(2): 468-479.
Johnston et al., (2008) Positron emission tomography using F-18 fluorodeoxyglucose pre- and post-autologous stem cell transplant in non-Hodgkin's lymphoma. Bone Marrow Transplant 41(11): 919-25.

Junghans et al (1990)Ant-Ta-H a humanized antibody to the intereukin 2 recepor with new features for immunotherapy in malignant and immune disorders. Cancer Res 50: 1495-1502.
Kasai et al., (1980) A glycolipid on the surface of mouse natural killer cells. Eur J Immunol 10(3): 175-80.
Kettleborough et al (1993)Optimizton of primes for cloning libraries of mouse immunogobulin genes using the polymerase chain reaction.Eur J Immunol 23(1): 206-211.
Kohler and Milstein (1975) Continuous cultures of fused cells secreting antibody of predefined specificity. Nature 256 (5517): 495-497.
MacCallum et al., (1996) Antibody-antigen interactions: contact analysis and binding site topography. J Mol Biol 262 (5): 732-745.
Marks et al., (1991) By-passing immunization. Human antibodies from V-gene libraries displayed on phage. J Mol Biol 222(3): 581-97.
Martin and Thornton (1996) Structural families in loops of homologous proteins: automatic classification, modelling and application to antibodies. J Mol Biol 263(5): 800-815.
Mellstedt (2000) Monoclonal antibodies as enhancers of the host's immunoresponse against the tumour. Annals of Oncology 11(3): 191-196.
O'Connor et al., (1998) Humanization of an antibody against human protein C and calcium-dependence involving framework residues. Protein Engineering 11(4): 321-328.
Padlan (1989) Structure of an antibody-antigen complex: crystal structure of the HyHEL-10 Fab-lysozyme complex. Proc Natl Acad Sci USA 86(15): 5938-5942.
Padlan (1991) A possible procedure for reducing the immunogenicity of antibody variable domains while preserving their ligand-binding properties. Mol Immunol 28(4-5): 489-98.
Pardoll and Topalian (1998) Tthe ole of CD4+ T cel responses in antitumor immunity Curr Opin Immunol 10(5): 588-594.
Philip et al., (1995) Autologous bone marrow transplantation as compared with salvage chemotherapy in relapses of chemotherapy-sensitive non-Hodgkin's lymphoma. N Engl J Med 333(23): 1540-5.
Poulou et al., (2010) Unifying the predictive value of pretransplant FDG PET in patients with lymphoma: a review and meta-analysis of published trials. Eur J Nucl Med Mol Imaging 37(1): 156-62.
Quaglino et al (2005)The adjuvant Activity of BAT antibody enables DNA vaccination to inhibit the progession of established autochthonous Her-2/neu carcinomas in BALB/c mice. Vaccine 23(25): 3280-7.
Queen et al., (1989)A humanized antibody that binds to the intereukin 2 receptor. Proc Nat Aca Sci USA 86: 10029-10033.
Raiter et al., (1999) Activaton of lymphocytes by BAT and anti CTLA-4: comparison of binding to T and B cells. Immunol Lett 69(2):247-51.
Raiter et al., (2000)CD4+ T lymphocytes as a primary celluar target for BAT mAb stimuaton. Int Immunol 12(11): 1623-8.
Riechmann et al., (1988) Reshaping human antibodies for therapy. Nature 332(6162): 323-327.
Rudikoff (1982) Single amino acid substitution altering antigen-binding specificity. Proc Natl Acad Sci USA 79(6): 1979-1983.
Sadanaga et al., (1999) Local Secretion of IFN-[gamma] Induces an Antitumor Response: Comparison Between T Cells Plus IL-2 and IFN-[gamma] Transfected Tumor Cells. J Immunother 22(4): 315-323.
Samaras et al., (2013) Prognostic factors for survival in lymphoma patients after autologous stem cell transplantation. Swiss Med Wkly 143: w13791: 1-16.
Sehn et al., (2005) Introduction of combined Chop plus rituximab therapy dramatically improved outcome of diffuse large B-cell lymphoma in British Columbia. J Clin Oncol 23(22): 5027-33.
Stemmer (1995) Single-step assembly of a gene and entire plasmid from large numbers of oligodeoxyribonucleotides. Gene 164(1): 49-53.
Studnicka et al., (1994) Human-engineered monoclonal antibodies retain full specific binding activity by preserving non-CDR complementarity-modulating residues. Protein Engineering 7(6): 805-814.
Sureda et al., (2001) Autologous stem-cell transplantation for Hodgkin's disease: results and prognostic factors in 494 patients from the

(56) References Cited

OTHER PUBLICATIONS

Grupo Español de Linfomas/Transplante Autólogo de Médula Osea Spanish Cooperative Group. J Clin Oncol 19(5): 1395-404.

Tan et al., (2002) "Superhumanized" antibodies: reduction of immunogenic potential by complementarity-determining region grafting with human germline sequences: application to an anti-CD28. The Journal of Immunology 169: 1119-1125.

Tramontano et al., (1990) Framework residue 71 is a major determinant of the positon and conformaton of the second hypervariable region in the VH domains of immunoglobulins, J Mol Biol 215(1): 175-182.

Trneny, M., et al.; Independent Predictive Value of PET-CT Pre Transplant in Relapsed and Refractory Patients with CD20 Diffuse Large B-Cell Lymphoma (DLBCL) Included in the CORAL Study; Program and abstracts of the 51st American Society of Hematology Annual Meeting and Exposition; Dec. 5-8, 2009; New Orleans, LA. Abstract 881.

Welte et al., (1984) Defective interleukin 2 production in patients after bone marrow transplantation and in vitro restoration of defective T lymphocyte proliferation by highly purified interleukin 2. Blood 64(2): 380-385.

\* cited by examiner

PIDILIZUMAB MONOCLONAL ANTIBODY THERAPY FOLLOWING STEM CELL TRANSPLANTATION

CROSS-REFERENCE TO RELATED APPLICATIONS

This application is claims the benefit of U.S. provisional application No. 61/901,015 filed Nov. 7, 2013, the entire content of which is incorporated herein by reference thereto.

FIELD OF INVENTION

The present invention relates to the field of cancer immunotherapeutics, and particularly to treatment of specific populations of cancer patients by administering an immunostimulatory antibody after stem cell transplantation.

SEQUENCE LISTING

The disclosure contains a Sequence Listing which has been submitted in ASCII format via EFS-Web and is hereby incorporated by reference in its entirety. The ASCII copy, created Nov. 7, 2014, is named 85189-22600-Sequence-Listing.txt and is 19,893 bytes in size.

BACKGROUND OF THE INVENTION

Cancer immunotherapeutics are aimed by and large at modulating the response of the immune system to induce or enhance killing of tumor cells. This approach utilizes using various immunomodulators including monoclonal antibodies that selectively bind to a specific determinant on T cells, thereby either initiating an activation pathway or inducing an inhibitory effect.

The main tumor-cell-killing effector cells are cytotoxic T lymphocytes, though accumulating evidence suggests that T-helper cells are also essential for priming the immune system against tumors. T-helper cells activate nonspecific immune effector mechanisms in the course of tumor destruction by secreting appropriate cytokines such as interferon-gamma among others.

BAT (also referred to as mBAT-1 or BAT-1) is a monoclonal antibody that was generated against a membrane preparation of a Burkitt lymphoma cell line (Daudi) and exhibits anti-tumor and immunostimulatory effects towards various types of tumors (Hardy et al., 2001, Int. J. Oncol. 19:897). BAT monoclonal antibody was disclosed in U.S. Pat. No. 5,897,862 to Hardy et al., which is incorporated in its entirety by reference, as is fully set forth herein. The polynucleotide and amino-acid sequences of murine BAT are disclosed in WO 00/58363, to Hardy et al., and U.S. Pat. No. 7,695,715, both publications incorporated herein by reference.

The BAT anti-tumor activity was studied in SCID (severe combined immunodeficiency disease) mice, beige mice that are deficient in NK cells and nude mice that are deficient in T cells (Hardy, B., 1997, Proc. Natl. Acad. Sci. USA 94:5756). All mice were injected i.v. with murine B16 melanoma cells and subsequently developed tumors in the lungs. BAT exerted an anti-tumor effect in SCID mice that were engrafted with either murine or human lymphocytes. In the athymic nude mice and the beige mice BAT exerted an anti-tumor activity, though this activity was less effective as compared to the anti-tumor activity of BAT in the wild-type mice.

The immunomodulatory effect of BAT was studied in vitro as well. Murine BAT activated $CD4^+$ T cells and induced the secretion of IFN-γ from these cells (Hardy et al., 2000, Int. Immunol. 12:1623 and Quaglino E. et al., 2005, Vaccine 9:23(25):3280-7, respectively). In addition. Hardy et al. showed that BAT triggers the proliferation of T cells and increases their cytolytic activity (Hardy, B. et al., 1997, Hum. Antibodies, 8:95).

U.S. Pat. No. 7,332,582 discloses humanized monoclonal antibodies termed hBAT-1, comprising the complementarity-determining regions (CDRs) of murine monoclonal antibody BAT-1, e.g. the antibody having the nonproprietary name pidilizumab.

U.S. Patent Application Publication No. 2009/0123413 relates to the use of the immunostimulatory pidilizumab monoclonal antibody for treatment of a variety of immunodeficiency related diseases and disorders and malfunction or incompetence of the immune system.

U.S. Pat. No. 8,747,847 relates to methods for inhibiting tumor growth, increasing survival of a subject having a tumor and inducing protection against tumor recurrence in a mammal, the methods comprise administering a humanized monoclonal antibody comprising CDR regions derived from the mBAT-1 murine monoclonal antibody, e.g. pidilizumab, in combination with at least one chemotherapeutic agent. U.S. Pat. No. 8,686,119 provides modified antibodies or fragments thereof having specific amino acid modifications compared to hBAT-1, humanized monoclonal immunomodulatory BAT-1 antibody (e.g. pidilizumab). Further provided were pharmaceutical compositions comprising said modified antibodies, and use thereof for the treatment of a variety of indications, particularly cancer and immunodeficiency disorders.

Autologous hematopoietic stem cell transplantation (ASCT or AHSCT) or high-dose autologous stem cell transplantation (HD-ASCT) have been shown to be the best available treatment in patients who have relapsed from non-Hodgkin's lymphoma (NHL) after conventional chemotherapy, but who remained chemotherapy-sensitive (Philip T. et al. New Engl J Med, 1995; 333: 1540-1545). ASCT is usually administered following an additional chemotherapeutic treatment, also termed "salvage chemotherapy". ASCT is also a preferable treatment in Hodgkin's lymphoma (Hodgkin's disease, HD) patients (Sureda A. et al. J Clin Oncol. 2001 Mar. 1; 19(5):1395-404). Patients for which ASCT is not recommended may undergo other stem cell transplantation procedures including allogeneic stem cell transplantation.

Metabolic imaging allows the recognition of an active tumor mass by identifying regions exhibiting increased metabolic activity. Metabolic imaging methods using (67) gallium, known as Ga-scan or Ga imaging, or (18)fluorodeoxyglucose (FDG), known as PET scan. PET imaging or FDG-PET, have often been employed for patients with Hodgkin's disease and non-Hodgkin lymphoma (Coiffier B., Curr Oncol Rep. 2001 May; 3(3):266-70).

Interestingly, it was demonstrated that FDG-PET imaging performed after salvage chemotherapy and prior to stem cell transplantation is predictive of the treatment outcome of NHL patients treated by high-dose chemotherapy and autologous stem cell transplantation (Cremerius et al. Bone Marrow Transplantation 2002(30), 103-111; Alousi A M et al. Br J Haematol. 2008 September; 142(5):786-92). Similar results were obtained in a study which investigated the predictive value of FDG-PET imaging prior to treatment with high dose chemotherapy and stem cell transplantation in 16 patients, including 10 NHL patients and six Hodgkin's disease patients (Becherer et al. Leukemia 2002; 16: 260-267).

Poulou et al. performed a meta-analysis of published trials involving FDG-PET scans obtained prior to ASCT in lymphoma patients (Poulou et al. Eur J Nucl Med Mol Imaging. 2010 January; 37(1):156-62). The meta-analysis found that FDG-PET scans following second-line chemotherapy (also termed "salvage chemotherapy") and before ASCT have significant prognostic value with respect to progression-free survival (PFS) and overall survival (OS) rates. The study confirmed that the survival rates of malignant lymphoma patients which had a positive pre-transplant PET scan result are significantly worse than those of patients who had a negative PET result. Although there was a clinical heterogeneity between the lymphoma types in the different studies analyzed by Poulou el al, no statistical heterogeneity was found between the studies and thus a positive pre-transplant FDG PET scan was concluded to be a uniform measure of progression and survival rates following ASCT in lymphoma patients.

Recently, Armand et al. reported the progression-free and overall survival rates of 105 patients with diffuse large B-cell lymphoma (DLBCL) who underwent autologous stem-cell transplantation in the last decade. Among this cohort, the survival rate of 46 patients who were chemosensitive but had a positive FDG-PET scan after salvage chemotherapy was examined. In this group, the 18-month post-transplant progression free survival PFS was 52% (90% CI, 0.39 to 0.63) (Armand P. et al., Br J Haematol., 160: 608-617, 2013).

A recent study in DLBCL patients assessed the predictive value of PET imaging or Ga imaging (PET/G) on the survival rates following ASCT. The study found that evidence of disease on PET/G scanning prior to transplantation is associated with an increased risk for relapse after ASCT (Alousi A M et al., Br J Haematol 142:786-792, 2008).

An international Phase II Trial (registered at clinicaltrials.gov under NCT-00532259) was designed to test the safety and effectiveness of the monoclonal antibody pidilizumab in patients with several types of non-Hodgkin lymphomas (e.g., diffuse large B cell lymphoma, transformed follicular lymphoma, diffuse mixed cell lymphoma and mediastinal large cell lymphoma), who received autologous peripheral blood stem cell transplantation (Armand et al., J. Clin. Oncol., 31(33):4199-206, 2013).

There is an unmet need for methods for increasing progression free survival as well as overall survival of cancer patients, including but not limited to lymphoma patients, following stem cell transplantation. In particular, in the rituximab era, the prognosis of patients with relapsed or refractory disease is poor. New therapies are therefore needed to increase the success rate of AHSCT, particularly in patients classified as positive for active disease prior to transplantation by means of metabolic imaging (e.g., PET) which are known to have a poor survival rate.

SUMMARY OF THE INVENTION

The present invention provides methods of treating cancer in specific patient populations among those suffering from cancer following stem cell transplantation, namely patients classified as positive by metabolic imaging prior to transplantation.

The present invention is based, in part, on the unexpected discovery that administration of the pidilizumab monoclonal antibody is a viable therapeutic strategy in the high-risk subset of cancer patients who undergo stem-cell transplantation, have residual disease and are classified as positive using a pre-transplant metabolic imaging such as PET scan. Thus, the present invention provides methods of treatment for patients otherwise considered to have an expected poor clinical outcome, namely a high risk of disease progression or death.

As used herein, a "metabolic imaging" or a "metabolic imaging method" refers to any method which allows the recognition of rapidly dividing cells (such as tumor cells or inflammatory cells) based on the increased metabolic activity in those cells. Metabolic imaging includes, but is not limited to, a Positron Emission Tomography (PET) imaging, possibly using Fludeoxyglucose 18F (FDG); or metabolic imaging using Gallium 67 (GA). The methods comprise administering an antibody, such as pidilizumab (a humanized BAT monoclonal antibody). Based on the results of the pre-transplant metabolic imaging, the patient can be classified as "positive by a pre-transplant metabolic imaging" if the results show active disease, or as "negative by a pre-transplant metabolic imaging" if the results do not show active disease. According to some embodiments, a patient which is classified as positive by a pre-transplant metabolic imaging is a subject having tumor cancer cells exhibiting increased metabolic activity as compared to the patient's healthy cells.

According to one aspect, the present invention provides a method of treating cancer in a human subject suffering from cancer and requiring stem cell transplantation, comprising the steps of: performing a pre-transplant metabolic imaging; classifying the patient as positive by the metabolic imaging; administering following stem cell transplantation to the subject a therapeutically effective amount of a pidilizumab monoclonal antibody or a fragment thereof comprising a light chain variable region comprising CDRs having the sequences SEQ. ID NO. 13. SEQ. ID NO. 14 and SEQ. ID NO. 15 and a heavy chain variable region comprising CDRs having the sequences: SEQ. ID NO. 16, SEQ. ID NO. 17 and SEQ. ID NO. 18, so as to thereby treat cancer or extend progression-free or overall survival in the subject, wherein said subject is classified as positive by a pre-transplant metabolic imaging. Each possibility represents a separate embodiment of the present invention.

According to some embodiments, the present invention provides a method of treating cancer or enhancing survival in a human subject suffering from cancer following stem cell transplantation, the method comprising administering to the subject a therapeutically effective amount of pidilizumab monoclonal antibody or a fragment thereof so as to thereby treat cancer or enhance survival in the subject, wherein the subject is classified as positive by a pre-transplant metabolic imaging. Each possibility represents a separate embodiment of the present invention.

According to some embodiments, the pidilizumab monoclonal antibody comprises a light chain variable region as set forth in SEQ ID NO: 22 (BATRκ$_D$) and a heavy chain variable region as set forth in SEQ ID NO: 25 (BATRH$_C$).

According to some embodiments, treating cancer or enhancing survival is associated with an increase in the level of circulating lymphocytes selected from the group consisting of: CD14+PD-L1+. CD14+PD-L2+ and a combination thereof. Each possibility represents a separate embodiment of the present invention.

In some embodiments, the pidilizumab monoclonal antibody comprises a light chain variable region selected from the group consisting of: BATRκa (SEQ. ID NO. 19). BATRκb (SEQ ID NO. 20), BATRκc (SEQ. ID NO. 21), BATRκd (SEQ. ID NO. 22), and the heavy chain variable region is selected from the group consisting of: BATRHA (SEQ. ID NO. 23), BATRHB (SEQ. ID NO. 24), BATRHC (SEQ. ID NO. 25), BATRHD (SEQ. ID NO. 26) and BATRHE (SEQ. ID NO. 27).

In additional embodiments, the pidilizumab monoclonal antibody comprises a variable region selected from the group consisting of: BATRH$_A$/BATRκa (SEQ. ID NO. 23/SEQ. ID NO. 19), BATRH$_B$/BATRκa (SEQ. ID NO. 24/SEQ. ID NO. 19). BATRH$_B$/BATRκb (SEQ. ID NO. 24/SEQ. ID NO. 20), BATRH$_C$/BATRκb (SEQ. ID NO. 25/SEQ. ID NO. 20). BATRH$_B$/BATRκd (SEQ. ID NO. 24/SEQ. ID NO. 22), and BATRH$_C$/BATRκd (SEQ. ID NO. 25/SEQ. ID NO. 22).

According to some embodiments, the pidilizumab monoclonal antibody fragment is selected from the group of antibody fragments consisting of: Fab, Fab', F(ab')2, Fv; single-chain antibody molecules and multi-specific antibodies formed from antibody fragments. Each possibility represents a separate embodiment of the present invention.

In one embodiment, the stem cell transplantation is an autologous stem cell transplantation. In another embodiment, the stem cell transplantation is an allogeneic stem cell transplantation. In yet another embodiment, the stem cells for stem cell transplantation are derived from umbilical cord.

In some embodiments, the metabolic imaging is selected from PET imaging and Ga imaging. In one embodiment, the metabolic imaging is PET imaging. In another embodiment, the metabolic imaging is Ga imaging.

In some embodiments, said cancer is lymphoma. In some embodiments, the lymphoma is selected from Hodgkin's lymphoma and non-Hodgkin's lymphoma.

In some embodiments, the Hodgkin's lymphoma is selected from classical Hodgkin's lymphoma and nodular lymphocyte-predominant Hodgkin's lymphoma.

In other embodiments, the non-Hodgkin's lymphoma is selected from the group consisting of: Burkitt lymphoma, chronic lymphocytic leukemia/small lymphocytic lymphoma (CLL/SLL), diffuse large B-cell lymphoma (DLBCL), follicular lymphoma, immunoblastic large cell lymphoma, precursor B-lymphoblastic lymphoma, mantle cell lymphoma, mycosis fungoides, anaplastic large cell lymphoma, precursor T-lymphoblastic lymphoma, AIDS-Related Lymphomas, Angioimmunoblastic Lymphoma, Blastic NK-Cell Lymphoma, Cutaneous T-Cell Lymphoma, Enteropathy-Type T-Cell Lymphoma, Hepatosplenic Gamma-Delta T-Cell Lymphoma, Lymphoblastic Lymphoma. Marginal Zone Lymphoma, Nasal T-Cell Lymphoma, Pediatric Lymphoma, Peripheral T-Cell Lymphomas, Primary Central Nervous System Lymphoma, T-Cell Leukemias, Transformed Lymphomas, Treatment-Related T-Cell Lymphomas and Waldenstrom's Macroglobulinemia. Each possibility represents a separate embodiment of the present invention.

In some embodiments, said lymphoma is selected from the group consisting of: diffuse large B cell lymphoma, primary mediastinal B-cell lymphoma and transformed indolent B cell non-Hodgkin's lymphoma. Each possibility represents a separate embodiment of the present invention.

In some embodiments, the pidilizumab monoclonal antibody is administered via intravenous infusion or injection, optionally by a peripheral or a central line. Each possibility represents a separate embodiment of the present invention. According to some embodiments, the pidilizumab monoclonal antibody is administered via intravenous injection, In some embodiments, the pidilizumab monoclonal antibody is administered via intravenous infusion.

According to some embodiments, the pidilizumab monoclonal antibody is administered periodically. In another embodiment, the pidilizumab monoclonal antibody is administered periodically according to an administration regime selected from the group consisting of: between 1-30 times within a period of 24 months following the stem cell transplantation; administration between 1-30 times within a period of 18 months following the stem cell transplantation; administration between 1-12 times within a period of 18 months following the stem cell transplantation; administration at least 3 times within a period of 18 months following the stem cell transplantation; administration of 3 times within a period of 18 months following the stem cell transplantation; administration of 3 times within a period of 18 weeks; administration 3 times within a period of 12 weeks; administration of 6 times within a period of 24 weeks; administration of 12 times within a period of 24 weeks; administration of 12 times within a period of 48 weeks: and administration of 27 times within a period of 54 weeks. Each possibility represents a separate embodiment of the present invention.

According to another embodiment, the first administration of the antibody is within 2-12 weeks after the stem cell transplantation. According to another embodiment, the first administration of the antibody is within 4-12 weeks after the stem cell transplantation. According to another embodiment, the periodic administration is every two-six weeks. According to one embodiment, the periodic administration is every about six weeks. According to another embodiment, the periodic administration is every about four weeks. According to another embodiment, the periodic administration is every about two weeks.

According to some embodiments, the first administration of the antibody is at least about 2 weeks following the stem cell transplantation. According to some embodiments, the first administration of the antibody is at least about 30 days following the stem cell transplantation.

According to some embodiments, the first administration of the antibody is at least 30 days following the last administration of a chemotherapeutic agent to the subject. According to some embodiments, the first administration of the antibody is between about 30-90, possible about 30-120 days following the last administration of a chemotherapeutic agent to the subject. Each possibility represents a separate embodiment of the present invention.

According to some embodiment, the therapeutically effective amount of pidilizumab monoclonal antibody is 1-6 mg/kg. In one embodiment, the therapeutically effective amount is 1 mg/kg. In another embodiment, the therapeutically effective amount is 1.5 mg/kg. In another embodiment, the therapeutically effective amount is 3 mg/kg. In yet another embodiment, the therapeutically effective amount is 6 mg/kg.

According to additional embodiments, the subject is diagnosed as having a measurable disease after the stem cell therapy.

According to another embodiment, the method further comprises administering at least one additional anti-cancer agent selected from the group consisting of: an anti-metabolic agent, an anti-angiogenic agent, a cytotoxic agent, anti-tumor therapeutic antibodies, cell based therapies and combinations thereof. Each possibility represents a separate embodiment of the present invention. According to another embodiment, the therapeutically effective amount of pidilizumab monoclonal antibody and said at least one therapeutic agent are administered together or sequentially. Each possibility represents a separate embodiment of the present invention. According to one embodiment the anti-tumor therapeutic antibody is Rituxan (also known as Rituximab).

Other objects, features and advantages of the present invention will become clear from the following description and drawings.

BRIEF DESCRIPTION OF THE FIGURES

(FIG. 1A) Survival rates for all treated patients (N=72); (FIG. 1B) Survival rates for all eligible patients (N=66).

DETAILED DESCRIPTION OF THE INVENTION

Figure 1A:
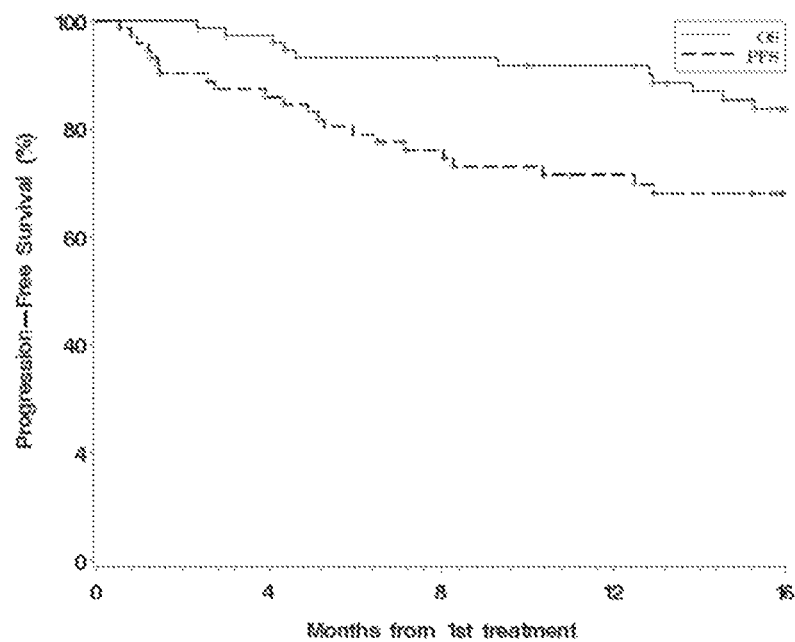
FIGS. 1A-B Show Kaplan-Meier models depicting overall survival (OS; continuous line) and progression-free survival (PFS; segmented line) in a patient population over time from the first administration of pidilizumab following autologous stem cell transplantation (ASCT).

According to some aspects, the present invention provides a method of treating cancer, including but not limited to lymphoma, in a subset of human subjects suffering from cancer following stem cell transplantation, the method comprising periodically administering to the subject a therapeutically effective amount of pidilizumab monoclonal antibody, wherein the subject is classified as positive for active disease prior to transplantation by means of metabolic imaging.

The present invention is based in part on the surprising finding that progression-free survival (PFS) and Overall survival (OS) rates were essentially identical in patients treated with pidilizumab monoclonal antibody following ASCT, independent of whether the patients were classified as PET-positive or PET negative prior to ASCT. As exemplified herein below, the PFS was 69% among patients treated with humanized BAT monoclonal antibody (pidilizumab) which were PET-positive prior to ASCT. Conversely, Armand et al. demonstrated that a patient population of 46 chemosensitive DLBCL patients who were classified as PET positive before stem-cell transplantation exhibited an 18-month post-ASCT progression free survival rate of 52% (Armand et al., Br J Haematol. 2013).

According to one aspect, the present invention provides a method of treating cancer in a human subject suffering from cancer and requiring stem cell transplantation, comprising the steps of: performing a pre-transplant metabolic imaging; classifying the patient as positive by the metabolic imaging: administering following stem cell transplantation to the subject a therapeutically effective amount of a pidilizumab monoclonal antibody or a fragment thereof comprising a light chain variable region comprising CDRs having the sequences SEQ. ID NO. 13, SEQ. ID NO. 14 and SEQ. ID NO. 15 and a heavy chain variable region comprising CDRs having the sequences: SEQ. ID NO. 16, SEQ. ID NO. 17 and SEQ. ID NO. 18, so as to thereby treat cancer or extend progression-free or overall survival in the subject, wherein said subject is classified as positive by a pre-transplant metabolic imaging. Each possibility represents a separate embodiment of the present invention.

According to some embodiments, the present invention provides a method of treating cancer or enhancing survival in a human subject suffering from cancer following stem cell transplantation, the method comprising administering to the subject a therapeutically effective amount of pidilizumab monoclonal antibody or a fragment thereof so as to thereby treat cancer or enhance survival in the subject, wherein the subject is classified as positive by a pre-transplant metabolic imaging. Each possibility represents a separate embodiment of the present invention.

According to some embodiments, the present invention provides a method of treating cancer or enhancing survival in a human subject suffering from cancer following stem cell transplantation, comprising administering to the subject a therapeutically effective amount of a pidilizumab monoclonal antibody or a fragment thereof comprising a light chain variable region comprising CDRs having the sequences SEQ. ID NO. 13, SEQ. ID NO. 14 and SEQ. ID NO. 15 and a heavy chain variable region comprising CDRs having the sequences: SEQ. ID NO. 16, SEQ. ID NO. 17 and SEQ. ID NO. 18, so as to thereby treat cancer or enhance survival in the subject, wherein said subject is classified as positive by a pre-transplant metabolic imaging. Each possibility represents a separate embodiment of the present invention.

According to some embodiments, the present invention provides a method of treating cancer or enhancing survival in a human subject suffering from cancer following stem cell transplantation, comprising administering to the subject a therapeutically effective amount of a humanized BAT monoclonal antibody or a fragment thereof comprising a light chain variable region comprising CDRs having the sequences SEQ. ID NO. 13. SEQ. ID NO. 14 and SEQ. ID NO. 15 and a heavy chain variable region comprising CDRs having the sequences: SEQ. ID NO. 16, SEQ. ID NO. 17 and SEQ. ID NO. 18, so as to thereby treat cancer or enhance survival in the subject, wherein said subject is classified as positive by a pre-transplant metabolic imaging. Each possibility represents a separate embodiment of the present invention.

According to some embodiments, the antibody used according to the methods of the present invention is a BAT monoclonal antibody. As use herein, the term "BAT" or "BAT-1" is used in a broad sense and specifically covers a monoclonal antibody or an antigen binding fragment thereof, wherein the monoclonal antibody is secreted by the hybridoma cell line deposited at the Collection Nationale de Cultures de Microorganismes (CNCM), under Accession No. I-1397, or recognizes the same antigenic epitope as the antibody in the above, as fully disclosed in U.S. Pat. No. 5,897,862 herein incorporated by reference in its entirety including supplements; A monoclonal antibody as fully described in U.S. Patent Application Publication No. 2003/0026800 (incorporated herein in its entirety by reference including supplements). A humanized monoclonal antibody, as fully described in WO 03/099196 which is incorporated herein by reference in its entirety. According to some embodiments, the BAT monoclonal antibody or fragment thereof comprises a light chain variable region comprising CDRs having the sequences SEQ. ID NO. 13: SEQ. ID NO. 14 and SEQ. ID NO. 15 and a heavy chain variable region comprising CDRs having the sequences: SEQ. ID NO. 16; SEQ. ID NO. 17 and SEQ. ID NO. 18.

According to certain embodiments, the BAT monoclonal antibody is characterized as follows: an antibody having a heavy chain variable region encoded by the polynucleotide sequence set forth in SEQ ID NO. 1; an antibody having a heavy chain variable region as set forth in SEQ ID NO:2; an antibody having a light chain variable region encoded by the polynucleotide sequence set forth in SEQ ID NO. 3 and/or an antibody having a light chain variable region as set forth in SEQ ID NO: 4, as disclosed in U.S. Patent Application Publication No. 20030026800.

According to another embodiment, the BAT monoclonal antibody is a humanized antibody. As used herein, the term "humanized antibody" refers to an antibody comprising a framework region from a human antibody and one or more complementarity determining regions (CDRs) from a non-human (usually a mouse or rat) immunoglobulin. Parts of a humanized immunoglobulin, except possibly the CDRs, are substantially identical to corresponding parts of natural human immunoglobulin sequences. Importantly, the humanized antibody is expected to bind to the same antigen as the donor antibody that provides the CDRs. The terms "framework region", "frame region" and "FR", as used herein, are used interchangeably and refer to variable domain residues of an antibody which are other than the hypervriable region residues. The term "hypervariable region" as used herein refers to amino acid residues of an antibody responsible for antigen binding, comprising amino acid residues of a complementarity determining region (CDR).

According to some embodiments, the frame regions of the light chain variable region in the humanized antibody are derived from the light chain variable region of the human TEL9 antibody. According to yet another specific embodiment, said frame regions are selected from the group consisting of: SEQ. ID NO. 5; SEQ. ID NO. 6; SEQ. ID NO. 7 and SEQ. ID NO. 8. According to another embodiment, the frame regions of the heavy chain variable region in the humanized antibody are derived from the heavy chain variable region of the human hsighv1295 antibody. According to another specific embodiment, said frame regions are selected from the group consisting of: SEQ. ID NO. 9; SEQ. ID NO. 10; SEQ. ID NO. 11 and SEQ. ID NO. 12.

Human TEL-9 antibody was identified in diverse libraries of immunoglobulin heavy (VH) and light (V kappa and V lambda) chain variable (V) genes prepared from peripheral blood lymphocytes of unimmunized donors (Marks et al. J Mol Biol. 1991, 222:581-97). This antibody was shown to bind specifically to the turkey egg-white lysozyme (TEL) antigen. Human hsiggv1295 antibody was isolated from stable hybridomas and Epstein-Barr virus-transformed B cell lines from the synovial fluid or peripheral blood of three patients with rheumatoid arthritis and one patient with systemic lupus erythematosus (Fang et al., J Exp Med. 1994, 179:1445-56).

According to some embodiments, the light chain variable region of the humanized BAT monoclonal antibody is selected from the group consisting of: BATRκa (SEQ. ID NO. 19). BATRκb (SEQ. ID NO. 20), BATRκ$_c$ (SEQ. ID NO. 21), BATRκ$_d$ (SEQ. ID NO. 22) and the heavy chain variable region is selected from the group consisting of: BATRH$_A$ (SEQ. ID NO. 23), BATRH$_B$ (SEQ. ID NO. 24), BATRHC (SEQ. ID NO. 25). BATRH$_D$ (SEQ. ID NO. 26) or BATRH$_E$ (SEQ. ID NO. 27). Each possibility represents a separate embodiment of the present invention.

According to some embodiments, the humanized BAT monoclonal antibody comprises a variable region selected from the group consisting of: BATRH$_A$/BATRκ$_a$ (SEQ. ID NO. 23/SEQ. ID NO. 19). BATRH$_B$/BATRκ$_a$ (SEQ. ID NO. 24/SEQ. ID NO. 19). BATRH$_B$/BATRκ$_b$ (SEQ. ID NO. 24/SEQ. ID NO. 20). BATRH$_C$/BATRκ$_b$ (SEQ. ID NO. 25/SEQ. ID NO. 20), BATRH$_B$/BATRκ$_d$ (SEQ. ID NO. 24/SEQ. ID NO. 22), or BATRH$_C$/BATRκ$_d$ (SEQ. ID NO. 25/SEQ. ID NO. 22). Each possibility represents a separate embodiment of the present invention.

According to some embodiments, the BAT humanized monoclonal antibody has a light chain variable region as set forth in SEQ ID NO: 22 (BATRκ$_D$) which may be encoded by the polynucleotide sequence set forth in SEQ ID NO: 28. According to some embodiments, the humanized BAT monoclonal antibody has a heavy chain variable region as set forth in SEQ ID NO: 25 (BATRH$_C$) which may be encoded by the polynucleotide sequence set forth in SEQ ID NO: 29.

According to another embodiment, the BAT monoclonal antibody is selected from the group consisting of: full length monoclonal antibody, chimeric antibody, humanized antibody, IgG, IgM, IgD, IgA. IgE, diabody, bispecific antibody, linear antibody and fragments thereof. Each possibility represents a separate embodiment of the present invention.

According to some embodiments, the humanized BAT monoclonal antibody is pidilizumab. As used herein, the term "pidilizumab" refers to a humanized BAT monoclonal antibody comprising a light chain variable region comprising CDRs having the sequences SEQ. ID NO. 13; SEQ. ID NO. 14 and SEQ. ID NO. 15 and a heavy chain variable region comprising CDRs having the sequences: SEQ. ID NO. 16; SEQ. ID NO. 17 and SEQ. ID NO. 18.

According to some embodiments, the pidilizumab monoclonal antibody is a humanized BAT antibody having a light chain variable region characterized by the formula:

$$FR_{L1}\text{-}CDR_{L1}\text{-}FR_{L2}\text{-}CDR^{L2}\text{-}FR_{L3}\text{-}CDR_{L3}\text{-}FR_{L4}$$

wherein the FRs are derived from the light chain variable region of the human TEL9 antibody and consist of: $FR_{L1}$, [EIVLT QSPSS LSASV GDRVT ITC; SEQ. ID NO. 5]; $FR_{L2}$, [W (F or Y) QQKPG KAPKL (W or L) TY; SEQ. ID NO. 6]; $FR_{L3}$, [GVPSR FSGSG SGT (D or S) (Y or F) (C or T) LTINS LQPED FATYY C; SEQ. ID NO. 7]; $FR_{L4}$, [FGGGT KLEIK; SEQ. ID NO. 8], and having a heavy chain variable region characterized by the formula:

$$FR_{H1}\text{-}CDR_{H1}\text{-}FR_{H2}\text{-}CDR_{H2}\text{-}FR_{H3}\text{-}CDR_{H3}\text{-}FR_{H4}$$

wherein the FRs are derived from the heavy chain variable region of the human hsigv1295 antibody and consist of:

$FR_{H1}$, [Q (I or V) QLV QSGSE LKKPG ASVKI SCKAS GY (T or S) F (T or S); SEQ. ID NO. 9]; $FR_{H2}$, [WV (R or K) QAPGQ GL (Q or K) WMG; SEQ. ID NO. 10]; $FR_{H3}$, [RF (V or A) FSLDT SV (N or S) TAYLQ ITSL (T or N) AEDTG MYFC (V or A) (R or K); SEQ. ID NO. 11]; $FR_{H4}$, [WGQGT LVTVS S; SEQ. ID NO. 12], and wherein the CDRs are derived from the murine BAT-1 antibody (the subscripts "L" and "H" refer to light and heavy chain regions, respectively) and consist of: $CDR_{L1}$ [SARSS VSYMH; SEQ. ID NO. 13]; $CDR_{L2}$ [RTSNL AS; SEQ. ID NO. 14]; $CDR_{L3}$ [QQRSS FPLT; SEQ. ID NO. 15]; $CDR_{H1}$ [NYGMN; SEQ. ID NO. 16]; $CDR_{H2}$ [WINTD SGEST YAEEF KG; SEQ. ID NO. 17]; $CDR_{H3}$ [VGYDA LDY; SEQ. ID NO. 18], as disclosed in International Patent Application, Publication No. WO 03/099196.

According to some embodiments, pidilizumab is a humanized monoclonal BAT antibody comprising a light chain variable region as set forth in SEQ ID NO: 22 ($BATR\kappa_D$) and a heavy chain variable region as set forth in SEQ ID NO: 25 ($BATRH_C$).

The term "antibody" is used in the broadest sense and specifically covers monoclonal antibodies (including full length monoclonal antibodies) of any of the classes IgG, IgM, IgD, IgA, IgE and antibody fragments so long as they exhibit the desired biological activity. "Antibody fragments" comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multi-specific antibodies formed from antibody fragments.

The term "monoclonal antibody" as used herein refers to antibodies that are highly specific, being directed against a single antigenic epitope. Alternatively, the term "monoclonal antibody" as used herein refers to an antibody produced from a single spleen cell clone. The monoclonal antibodies to be used in accordance with the present invention may be made by recombinant DNA methods (see, e.g., U.S. Pat. No. 5,225,539 to Winter and U.S. Pat. No. 5,530,101 to Queen et al.).

In accordance with one embodiment of the invention, the monoclonal antibody is a chimeric human-mouse antibody, namely a mAb with a constant region derived from a human origin and a variable region derived from mouse. For this purpose, the Kappa light and heavy chain variable regions of the mAb of the invention were PCR cloned and their DNA sequenced.

In accordance with yet another embodiment of the invention, the antibody is a fully humanized antibody, i.e. the framework regions of the variable region and the constant region are derived from a human source.

The term "diabody" refers to a dimeric antibody fragment. In each polypeptide, a heavy-chain variable domain (VH) is linked to a light-chain variable domain (VL) but unlike single-chain Fv fragments, each antigen-binding site is formed by pairing of one VH and one VL domain from the two different polypeptides. Diabodies thus have two antigen-binding sites, and can be bispecific.

The term "bispecific antibody" refers to an antibody that is able to specifically bind to two different molecules. Binding of a bispecific antibody to a first molecule takes place with one F(ab') binding arm, and binding to a second molecule, such as a tumor-specific antigen on a tumor cell, takes place with another F(ab') binding arm. A bispecific antibody may further bind an FcR via its Fc portion.

The administration of the compositions of the present invention can be typically achieved by means of parenteral administration, e.g., intravenously (i.v.) intraperitoneally (i.p.) subcutaneously (s.c.) or intramuscularly (i.m.) or intradermally (i.d.). In exemplary embodiments, the BAT monoclonal antibody is administered via intravenous injection. According to some embodiments, pidilizumab is administered by intravenous injection according to the methods of the present invention. Methods of treatment may comprise pharmaceutical compositions of pidilizumab according to the invention.

According to some embodiments, the pidilizumab monoclonal antibody according to the present invention is formulated as the active ingredient in a pharmaceutical composition comprising a pharmaceutically acceptable excipient or carrier. Each possibility is a separate embodiment of the present invention. Preferably, the composition of the present invention has a form suitable for injections. The pharmaceutical composition disclosed in this invention may further comprise any pharmaceutically acceptable diluent or carrier to provide a physiologically acceptable conjugates comprising BAT or pidilizumab with one or more therapeutic agents. Each possibility is a separate embodiment of the present invention.

The pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes. Preferably, the pharmaceutical compositions of the present invention may be manufactured by processes that are particularly suitable for proteins, more particularly antibodies.

Pharmaceutical compositions for use in accordance with the present invention may be formulated in conventional manner using one or more physiologically acceptable carriers comprising excipients and auxiliaries, which facilitate processing of the active compounds into preparations and that are pharmaceutically suitable. Proper formulation is dependent upon the route of administration chosen.

For injection or infusion, the compounds of the invention may be formulated in aqueous solutions, preferably in physiologically compatible buffers such as Hank's solution, Ringer's solution, or physiological saline buffer.

Pharmaceutical compositions for parenteral administration may include aqueous solutions of the active ingredients, namely the monoclonal antibody of the invention, in water-soluble form. Additionally, suspensions of the active compounds may be prepared as appropriate oily injection suspensions. Suitable natural or synthetic carriers are well known in the art. Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile pyrogen-free water, before use.

Pharmaceutical compositions for use in accordance with the present invention may be formulated for delivery via inhalation in a manner using one or more physiologically acceptable carriers comprising excipients and auxiliaries, which facilitate processing of the active compounds into preparations that are pharmaceutically suitable.

Pharmaceutical compositions suitable for use in context of the present invention may include compositions wherein the active ingredient, namely the antibody of the invention, is contained in an amount effective to achieve the intended purpose. All formulations for administration should be in dosages suitable for the chosen route of administration. The term "effective amount" should be understood as meaning an amount of an antibody of the invention required to achieve a therapeutic effect. More specifically, a therapeutically effective dose or amount means an amount of an antibody of the invention effective to prevent, alleviate or ameliorate symptoms of cancer of the subject being treated and/or effective in enhancing the survival rate of that subject. Each possibility represents a separate embodiment of the present invention. Determination of a therapeutically effective amount is well within the capability of those skilled in the art, especially in light of the detailed disclosure provided herein. According to some embodiments, a therapeutically effective amount of an antibody composition according to the present invention is an amount sufficient to treat cancer and/or delay disease progression and/or enhance survival rate of a subject who is suffering from cancer following stem cell transplantation and who was diagnosed as positive by a pre-transplant metabolic imaging. Each possibility represents a separate embodiment of the present invention.

According to some embodiments, the dose of the antibody composition to be administrated to a subject, in the context of the present invention should be sufficient to affect a beneficial therapeutic response in the subject over time, or to induce lymphopoiesis and/or proliferation, activation, removal/abolishment of inhibition, or differentiation of T cells, NK cells, NK-T cells, and B cells. Each possibility represents a separate embodiment of the present invention. According to some embodiments, the effect of the antibody composition may be the induction of lymphopoiesis and/or proliferation, activation, removal/abolishment of inhibition, or differentiation of cells, such as, T cells, NK cells, NK-T cells, Thy1.2 cells, B cells, monocytes, macrophages, transplanted stem cells derived from either the bone marrow, umbilical cord blood or peripheral blood or lymphocytes following donor leukocyte infusion. Each possibility represents a separate embodiment of the present invention.

The effective amount required to achieve the therapeutic end result may depend on a number of factors including, for example, the specific type of the disorder and the severity of the patient's condition, and whether the antibody is co-administered together with another agent which acts together with the antibody in an additive or synergistic manner. The dose of the administered composition may be determined by the activity of the therapeutic composition produced and the condition of the subject, as well as the body weight or surface area of the subject to be treated. The size of the administered dose and the dosing regimen may also be determined by the existence, nature, and extent of any adverse side effects that accompany the administration of the antibody composition of the invention in a particular subject. In determining the effective amount of the therapeutic composition to be administered, the physician may need to evaluate, inter alia, circulating plasma levels, toxicity, and progression of the disease.

Toxicity and therapeutic efficacy of the compositions described herein can be determined by standard pharmaceutical procedures in cell cultures or experimental animals, e.g., by determining the maximal tolerated dose. The data obtained from these cell culture assays and animal studies can be used in formulating a range of dosage for use in human. The dosage may vary depending inter alia upon the dosage form employed, the dosing regimen chosen, the composition of the agents used for the treatment and the route of administration utilized among other relevant factors. The exact formulation, route of administration and dosage can be chosen by the individual physician in view of the patient's condition. Depending on the severity and responsiveness of the condition to be treated, dosing can be a single or periodic administration. The amount of a composition to be administered will, of course, be dependent on the subject being treated, the severity of the affliction, the manner of administration, the judgment of the prescribing physician, and all other relevant factors.

According to some embodiments, the therapeutically effective amount is 0.2-18 mg/kg. According to some embodiments, the therapeutically effective amount is 0.5-4.5 mg/kg. According to some embodiments, the therapeutically effective amount is 1-2 mg/kg. In another embodiment, the therapeutically effective amount is 1 mg/kg. In another embodiment, the therapeutically effective amount is 1.5 mg/kg. In another embodiment, the therapeutically effective amount is about 1.5 mg/kg. In another embodiment, the therapeutically effective amount is about 3 mg/kg. In another embodiment, the therapeutically effective amount is about 4.5 mg/kg. In another embodiment, the therapeutically effective amount is about 6 mg/kg. In another embodiment, the therapeutically effective amount is about 12 mg/kg. In another embodiment, the therapeutically effective amount is about 18 mg/kg.

According to some embodiments, administration of the antibody according to the method of the invention is periodic administration. A "periodic administration" of a therapeutic effective amount, as used herein, refers to a recurring administration of the specified therapeutic effective amount. According to a non-limiting example, a periodic administration of a therapeutic effective amount of about 1.5 mg/kg, means that the patient is administered a dose of a composition comprising 1.5 mg/kg of the antibody of the invention for several times during a certain period. The periodic administration can be daily, every other day, weekly, every two weeks, every 4 weeks, every 6 weeks, or any other administration regime sufficient to affect a beneficial therapeutic response as disclosed herein. Each possibility represents a separate embodiment of the present invention. According to some embodiments, periodic administration is administration in constant intervals such as, but not limited to, every 2 weeks, every 30 days, every 42 days or every 45 days. Each possibility represents a separate embodiment of the present invention. According to some embodiments, the antibody of the invention is administered periodically every 42 days. According to some embodiments, at least 3 therapeutically effective amounts of the antibody of the invention are administered periodically every 42 days according to the method of the invention. According to other embodiments, periodic administration according to the methods of the invention comprises administration in varying intervals. According to some embodiments, the periodic administration is every about six weeks. According to another embodiment, the periodic administration is every about four weeks. According to yet another embodiment, the periodic administration is every about two weeks.

According to some embodiments, at least 2, 3, 4, 5 or 6 therapeutic effective amounts of the antibody of the invention are periodically administered according to the method of the invention. Each possibility represents a separate embodiment of the present invention. According to some embodiments, at least 3, 6, 12, or 24 therapeutic effective amounts of the antibody of the invention are periodically administered according to the method of the invention. Each possibility represents a separate embodiment of the present invention. According to some embodiments, at least 3 therapeutic effective amounts of the antibody of the invention are periodically administered according to the method of the invention. According to some embodiments, between 1-4 therapeutic effective amounts of the antibody of the invention are periodically administered according to the method of the invention. According to some embodiments, the antibody of the invention is pidilizumab. According to some embodiments, the antibody of the invention is humanized monoclonal BAT.

According to some embodiments, the antibody of the invention is periodically administered within a period of about 1-24 months. According to some embodiments, the antibody of the invention is periodically administered within a period of about 1-12 months. According to some embodiments, the antibody of the invention is periodically administered within a period of about 1-6 months. According to some embodiments, the antibody of the invention is periodically administered within a period of about 3-5 months. According to some embodiments, the antibody of the invention is periodically administered within a period of about 4 months.

According to one embodiment, the antibody is administered 3 times within a period of 12 weeks. According to another embodiment, the antibody is administered 6 times within a period of 24 weeks. According to yet another embodiment, the antibody is administered 12 times within a period of 24 weeks. According to some embodiments, the antibody is administered 12 times within a period of 48 weeks. According to an additional embodiment, the antibody is administered 27 times within a period of 54 weeks. According to an additional embodiment, the antibody is administered 54 times within a period of 108 weeks.

According to some embodiments, the antibody is administered to the subject following the stem-cell transplantation. According to some embodiments, the stem-cell transplantation is autologous hematopoietic stem cell transplantation. According to another embodiment, the first administration of the antibody is 2-12 weeks after the stem cell transplantation. According to some embodiments, a first therapeutically effective amount of the antibody of the invention is administered to the subject between 10-120 days following the stem-cell transplantation. According to some embodiments, a first therapeutically effective amount of the antibody of the invention is administered to the subject between 20-100 days following the stem-cell transplantation. According to some embodiments, a first therapeutically effective amount of the antibody of the invention is administered to the subject between 30-90 days following the stem-cell transplantation.

According to some embodiments, the antibody is administered according to the methods of the invention within a period of 24 months following the stem cell transplantation. According to some embodiments, the antibody is administered according to the methods of the invention within a period of 18 months following the stem cell transplantation. According to some embodiments, the antibody is administered according to the methods of the invention within a period of 12 months following the stem cell transplantation. According to some embodiments, the antibody is administered according to the methods of the invention within a period of 6 months following the stem cell transplantation.

According to some embodiments, the antibody is administered between 1-30 times within a period of 18 months following the stem cell transplantation. According to one embodiment, the antibody is administered between 1-12 times within a period of 18 months following the stem cell transplantation. According to another embodiment, the antibody is administered at least 3 times within a period of 18 months following the stem cell transplantation. According to one embodiment, the antibody is administered 3 times within a period of 18 months following the stem cell transplantation. According to another embodiment, the antibody is administered 3 times within a period of 18 weeks.

According to some embodiments, the subject to be treated according to the methods of the invention is a subject who is afflicted with cancer and is after stem cell transplantation and who is classified as positive by a pre-transplant metabolic imaging. According to another embodiment, the subject is diagnosed as having a measurable disease after the stem cell therapy. According to another embodiment, the subject to be treated is a subject diagnosed as having chemosensitive disease prior to the stem cell transplantation. As used herein "chemosensitive disease" refers to cancer which exhibited at least partial remission following administration of pre-transplant chemotherapy (also known as salvage treatment or salvage chemotherapy). Remission may be typically measured by CT scan. According to some embodiments, the subject to be treated is a subject which has been treated prior to stem-cell transplantation by at least one salvage treatment selected from the group consisting of: chemotherapy, radiation, biological treatment (such as, but not limited to, rituximab administration) and a combination thereof. Each possibility represents a separate embodiment of the present invention.

According to yet another embodiment, the subject to be treated received the antibody having the non-proprietary name Rituximab (also known as Rituxan or MabThera) as a first line cancer therapy and/or as a salvage therapy prior to stem-cell transplantation. Each possibility represents a separate embodiment of the present invention.

According to additional embodiments, the method of the invention further comprises administering at least one additional anti-cancer agent selected from the group consisting of: chemotherapeutic agent including, but not limited to, anti-metabolic agents, anti-angiogenic agents, and cytotoxic agents; anti-tumor therapeutic antibodies; cell based therapies and a combination thereof. Each possibility represents a separate embodiment of the present invention. According to a specific embodiment, the anti-tumor therapeutic antibody is rituximab. According to another embodiment, the cell based therapy is Provenge (also known as Sipuleucel-T). According to another embodiment, said therapeutically effective amount of pidilizumab monoclonal antibody and said at least one therapeutic agent are administered together or sequentially. According to some embodiments, the therapeutically effective amounts of pidilizumab and the at least one therapeutic agent are administered together or sequentially.

In some embodiments, the at least one additional anti-cancer agent is a chemotherapeutic agent selected from the group consisting of: antimetabolites, platinum-based agents, mitotic inhibitors, anthracycline antibiotics, topoisomerase inhibitors, anti-angiogenic agents and combinations thereof, as disclosed in U.S. Pat. No. 8,747,847, incorporated herein by reference in its entirety.

As used herein, a "metabolic imaging" or a "metabolic imaging method" refers to any method which allows the recognition of rapidly dividing cells (such as tumor cells or inflammatory cells) based on the increased metabolic activity in those cells, including the use of a tracer (such as a radioactive tracer) which is taken in greater amounts by rapidly dividing cells relative to normal tissues. Tracer types include but are not limited to a glucose analog and an iron analog, for example (18)fluorodeoxyglucose (FDG) tracer and (67)gallium. Metabolic imaging methods include but are not limited to Ga-scan (Ga imaging, gallium imaging) and PET scan (PET imaging). In one embodiment, the metabolic imaging is PET imaging. In some embodiments, the metabolic imaging is PET imaging using (18)fluorodeoxyglucose (FDG), also known as FDG-PET. In another embodiment, the metabolic imaging is Ga imaging.

The term "pre-transplant metabolic imaging" relates to the characterization, recognition, monitoring or staging a tumor using a metabolic imaging method before stem cell transplantation and after the finalization of a primary, secondary or salvage therapy, including but not limited to radiation or chemotherapy. The pre-transplant metabolic imaging may be performed before, during or after a conditioning therapy.

A "conditioning therapy" as used herein refers to therapy that is designed to be followed by stem cell transplantation, for example chemotherapy designed to prepare the patient for transplantation, aggressive therapy eradicating the patient's cancer cells and existing stem cells to create a clean environment for transplant, or aggressive therapy eradicating cancer cells and patient's stem cells, requiring stem cell transplantation in order to replenish the bone marrow.

Based on the results of the pre-transplant metabolic imaging, the patient can be classified as "positive by a pre-transplant metabolic imaging" if the results show active disease, or as "negative by a pre-transplant metabolic imaging" if the results do not show active disease. According to some embodiments, a patient which is classified as positive by a pre-transplant metabolic imaging is a subject having tumor cancer cells exhibiting increased metabolic activity as compared to the patient's healthy cells.

As used herein, "treating cancer in a subject suffering from cancer following stem cell transplantation" refers to the performance of the methods of the invention in a subject suffering from cancer (e.g., lymphoma) that had undergone stem cell transplantation about 30 to about 90 days prior to the performance of the methods of the invention. According to some embodiments, treating refers to elongating the overall survival (OS) and/or progression free survival (PFS) of the subject. Each possibility represents a separate embodiment of the present invention.

In some embodiments, the stem cell transplantation of the methods of the invention is autologous stem cell transplantation. In a particular embodiment, the stem cell transplantation is autologous hematopoietic stem cell transplantation (AHSCT). According to some embodiments, the autologous stem cell transplantation is high-dose autologous stem cell transplantation (or HD-ASCT). In an additional embodiment, the stem cell transplantation is allogeneic stem cell transplantation. In yet another embodiment, the stem cells are derived from the umbilical cord.

The subject to be treated according to the method of the invention is afflicted with cancer. According to some embodiments, the cancer is lymphoma. According to some embodiments, the lymphoma is selected from the group consisting of Hodgkin's lymphoma (or Hodgkin's disease) and non-Hodgkin's lymphoma. Each possibility represents a separate embodiment of the present invention.

Lymphoma occurs when lymphocytes, a type of white blood cell, grow abnormally. The body has two main types of lymphocytes that can develop into lymphomas: B-lymphocytes (B-cells) and T-lymphocytes (T-cells). Cancerous lymphocytes can travel to many parts of the body, including the lymph nodes, spleen, bone marrow, blood or other organs, and can accumulate to form tumors. There are two basic categories of lymphomas. One kind is Hodgkin's lymphoma, which is marked by the presence of a type of cell called the Reed-Sternberg cell. The other category is non-Hodgkin's lymphomas, which includes a large, diverse group of cancers of immune system cells. Non-Hodgkin lymphomas can be further divided into cancers that have an indolent (slow-growing) course and those that have an aggressive (fast-growing) course. These subtypes behave and respond to treatment differently. Both Hodgkin and non-Hodgkin lymphomas can occur in children and adults, and prognosis and treatment depend on the stage and the type of cancer.

In some embodiments, the methods and compositions of the present invention are useful in treating Hodgkin's lymphoma patients following stem cell transplantation, said patients being classified as positive for active disease by means of pre-transplant metabolic imaging.

The two major types of Hodgkin's lymphoma are classical Hodgkin's lymphoma and nodular lymphocyte-predominant Hodgkin's lymphoma (National Cancer Institute, www.cancer.gov/cancertopics/types/hodgkin). Symptoms include the painless enlargement of lymph nodes, spleen, or other immune tissue. Other symptoms include fever, weight loss, fatigue, or night sweats.

In some embodiments, the subject treated by the methods and compositions of the invention is suffering from Hodgkin's lymphoma. In particular embodiments, the Hodgkin lymphoma is selected from classical Hodgkin lymphoma and nodular lymphocyte-predominant Hodgkin lymphoma.

In exemplary embodiments, the methods and compositions of the present invention are particularly useful in treating the high-risk subset of non-Hodgkin's lymphoma patients following stem cell transplantation, said patients being classified as positive for active disease by means of pre-transplant metabolic imaging.

Non-Hodgkin's lymphoma (NHL) is the most common cancer of the lymphatic system. Non-Hodgkin's lymphoma is not a single disease, but rather a group of several closely related cancers. The World Health Organization estimates that there are at least 61 types of NHL. Although the various types of NHL have some things in common, they differ in their appearance under the microscope, their molecular features, their growth patterns, their impact on the body and how they are treated.

Common signs and symptoms of NHL include swelling of the lymph nodes (which is often but not always painless), fever, night sweats, unexplained weight loss and lack of energy.

The causes of NHL remain unknown, however, risk for developing lymphoma may be higher in individuals who have a family history of NHL (though no hereditary pattern has been well established), are affected with an autoimmune disease, have received an organ transplant, have been exposed to chemicals such as pesticides, fertil-izers or organic solvents for a long period, or have been infected with viruses such as Epstein-Barr, human T-lymphotropic virus type 1 (HTLV-1), HIV/AIDS, hepatitis C or certain bacteria, such as *H-pylori*.

Non-Hodgkin's lymphoma is divided into four stages based on how far the disease has spread: Stage I (early disease): the cancer is found only in a single lymph node; or in one organ or area outside the lymph node; Stage II (locally advanced disease): the cancer is found in two or more lymph node regions on one side of the diaphragm; Stage III (advanced disease): the cancer involves lymph nodes both above and below the diaphragm; Stage IV (widespread disease): the cancer is found in several parts of one or more organs or tissues (in addition to the lymph nodes), or is in the liver, blood or bone marrow.

Non-Hodgkin's lymphomas are also broadly divided into two major groups: B-cell lymphomas and T-cell lymphomas. B-cell lymphomas develop from abnormal B-lymphocytes and account for 85 percent of all NHLs. T-cell lymphomas develop from abnormal T-lymphocytes and account for the remaining 15 percent of all NHLs. In other embodiments, the subject is suffering from non-Hodgkin's lymphoma. According to some embodiments, non-Hodgkin's lymphoma is selected from the group consisting of: Burkitt lymphoma, chronic lymphocytic leukemia/small lymphocytic lymphoma (CLL/SLL), diffuse large B-cell lymphoma (DLBCL), follicular lymphoma, immunoblastic large cell lymphoma, precursor B-lymphoblastic lymphoma, mantle cell lymphoma, mycosis fungoides, anaplastic large cell lymphoma, precursor T-lymphoblastic lymphoma, AIDS-Related Lymphomas, Angioimmunoblastic Lymphoma, Blastic NK-Cell Lymphoma. Cutaneous T-Cell Lymphoma. Enteropathy-Type T-Cell Lymphoma, Hepatosplenic Gamma-Delta T-Cell Lymphoma, Lymphoblastic Lymphoma, Marginal Zone Lymphoma, Nasal T-Cell Lymphoma, Pediatric Lymphoma, Peripheral T-Cell Lymphomas, Primary Central Nervous System Lymphoma, T-Cell Leukemias, Transformed Lymphomas, Treatment-Related T-Cell Lymphomas and Waldenstrom's Macroglobulinemia (described in NCCN Guidelines on Non-Hodgkin's lymphoma, Version 3.2012; and National Cancer Institute, www.cancer.gov/cancertopics/types/hodgkin). Each possibility represents a separate embodiment of the present invention.

In some embodiments, the lymphoma is diffuse large B cell lymphoma (DLBCL). In another embodiment, the lymphoma is primary mediastinal B-cell lymphoma. In another embodiment, the lymphoma is transformed indolent B cell non-Hodgkin's lymphoma. In another embodiment, the lymphoma is transformed follicular lymphoma. In another embodiment, the lymphoma is diffuse mixed cell lymphoma. In yet another embodiment, the lymphoma is mediastinal large cell lymphoma.

In yet additional embodiments, the methods and compositions of the present invention have an anti-tumor effect in cancer patients following stem cell transplantation, said patients being classified as positive for active disease by means of pre-transplant metabolic imaging.

According to some embodiments, all types of tumors may be treated by the methods of the present invention. The tumors may be solid or non-solid. Some examples of solid tumors that can be treated according to the methods of the present invention include carcinomas, sarcomas, blastomas or gliomas. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, liver tumors, esophageal tumors and gastric tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Each possibility represents a separate embodiment of the present invention. Examples of vascularized skin cancers include squamous cell carcinoma, basal cell carcinoma and skin cancers that can be treated by suppressing the growth of malignant keratinocytes, such as human malignant keratinocytes.

In some embodiments, the type of cancer to be treated by the methods of the invention is selected from the group consisting of: colorectal carcinoma; lung carcinoma including non-small lung cancer (NSCLC) and small cell lung cancer (SCLC); breast carcinoma; melanoma; ovarian carcinoma; cervical carcinoma, pancreatic cancer; head and neck carcinoma; gastrointestinal carcinoma; esophageal tumors; hepatocellular carcinoma; renal cell carcinoma; prostate tumors; Kaposi's sarcoma; squamous cell carcinoma and basal cell carcinoma. Each possibility represents a separate embodiment of the present invention.

According to another aspect, the present invention provides use of pidilizumab monoclonal antibody in the manufacture of a medicament for treating cancer, including but not limited to lymphoma, in a human subject suffering from cancer, following stem cell transplantation, wherein the subject is classified as positive by a pre-transplant metabolic imaging.

According to another aspect, the present invention provides a method of inducing an immune response against cancer cells, including but not limited to lymphoma cells, in a subject suffering from cancer, including but not limited to lymphoma, following stem cell transplantation, comprising periodically administering to the subject a therapeutically effective amount of pidilizumab monoclonal antibody so as to thereby treat cancer, including but not limited to lymphoma, in the subject, wherein the subject is classified as positive by a pre-transplant metabolic imaging. According to some embodiments, the pidilizumab monoclonal antibody comprises a light chain variable region comprising CDRs having the sequences SEQ. ID NO. 13, SEQ. ID NO. 14 and SEQ. ID NO. 15 and a heavy chain variable region comprising CDRs having the sequences: SEQ. ID NO. 16, SEQ. ID NO. 17 and SEQ. ID NO. 18.

According to yet another aspect, the present invention provides use of pidilizumab monoclonal antibody in the manufacture of a medicament for inducing an immune response against cancer, including but not limited to lymphoma, in a human subject suffering from cancer, following stem cell transplantation, wherein the subject is classified as positive by a pre-transplant metabolic imaging.

According to an additional aspect, the present invention provides a pharmaceutical composition comprising a therapeutically effective amount of pidilizumab monoclonal antibody for use in treating cancer, including but not limited to lymphoma, in a human subject suffering from cancer, following stem cell transplantation, wherein the subject is classified as positive by a pre-transplant metabolic imaging.

According to a further aspect, the present invention provides a pharmaceutical composition comprising a therapeutically effective amount of pidilizumab monoclonal antibody for use in inducing an immune response in a human subject suffering from cancer, following stem cell transplantation, wherein the subject is classified as positive by a pre-transplant metabolic imaging.

The terms "comprises", "comprising", "includes", "including", "having" and their conjugates mean "including but not limited to". The terms "comprises" and "comprising" are limited in some embodiments to "consists" and "consisting", respectively. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure. In the description and claims of the application, each of the words "comprise" "include" and "have", and forms thereof, are not necessarily limited to members in a list with which the words may be associated.

As used herein, the singular form "a", "an" and "the" include plural references unless the context clearly dictates otherwise. For example, the term "a compound" or "at least one compound" may include a plurality of compounds, including mixtures thereof.

As used herein the term "about" refers to plus/minus 10% of the value stated.

Having now generally described the invention, the same will be more readily understood through reference to the following examples, which are provided by way of illustration and are not intended to be limiting of the present invention.

Examples

An international phase II clinical trial of pidilizumab monoclonal antibody was performed in NHL patients (including diffuse large B cell lymphoma, transformed follicular lymphoma, diffuse mixed cell lymphoma or mediastinal large cell lymphoma) after autologous peripheral blood stem cell transplantation (ASCT). The study was performed to assess the safety and effectiveness of the monoclonal antibody, pidilizumab, in patients with NHL who have received autologous peripheral blood stem cell transplantation.

Patients were recruited at 30 centers in the US, Israel, Chile and India. The study was approved by the Offices for Human Research Studies (or equivalent) at each of the participating institution, and conducted in accordance with the principles of the Declaration of Helsinki. It was registered at clinicaltrials.gov under NCT-00532259.

Patients, Treatment and Monitoring

Patients 18 years and older could enroll on this study if they had undergone ASCT for relapsed or refractory DLBCL, primary mediastinal B-cell lymphoma (PMBCL) or transformed indolent B-cell non-Hodgkin lymphoma (B-NHL). Generally, only patients with chemosensitive disease, defined as obtention of at least partial remission with their last pre-ASCT salvage therapy, measured by CT, were eligible. PET scanning was not required to demonstrate chemosensitivity. Disease progression was determined based on Cheson's criteria (Cheson B D., et al. J. Clin. Oncol 2007; 25 (5): 579-586. PMID: 17242396).

Patients could be registered pre- or post-ASCT. In either case, confirmatory screening was performed between 30 and 90 days after ASCT. To be eligible to proceed on study and receive treatment, patients had to have post-ASCT restaging within 30 to 90 days prior to first drug administration showing no evidence of tumor progression from pre-transplant assessment, as well as hematologic, renal, hepatic and cardiac function within the allowed range (WBC≥22.5×10$^9$/l, platelets ≥40×10$^9$/l, creatinine<1.5×upper limit of normal (ULN), bilirubin<1.5 mg/dl, AST/ALT<3×ULN, no NYHA class II or higher heart disease or arrhythmia requiring treatment). Patients with type 1 diabetes, known immune deficiency (including HIV infection) or active autoimmune disease, evidence of CNS involvement by lymphoma, or active infection (including hepatitis B or C with active viremia) were excluded.

Patients who passed the confirmatory screening received treatment with pidilizumab administered intravenously at a dose of 1.5 mg/kg every 42 days for up to 3 cycles. Pre-medication consisted of acetaminophen or ibuprofen, as well as diphenhydramine (50 mg IV) or promethazine (25 mg IV). No other anti-lymphoma treatment was allowed. Patients were restaged with CT scans, and optionally with PET scans (at the discretion of the treating clinicians) at the confirmatory screening, within 30 days before cycle 1, then before the $2^{nd}$ and $3^{rd}$ cycles, and then at 30, 44 and 69 weeks (from the $1^{st}$ day of treatment). Treatment was stopped if there was definite evidence of tumor progression based on standard criteria (Cheson B D, ibid.). Patients were followed until 16 months (69 weeks) from start of treatment (corresponding to about 18 months from ASCT). Safety data was reviewed by the Data and Safety Monitoring Board after the first 10, 20 and 40 patients completed study treatment.

Ninety-seven patients were screened (pre- or post-ASCT) for this study. Of those, 72 patients were included in the treated analysis set and received at least 1 dose of pidilizumab (treated subset) at a median of 2.6 months after ASCT (range, 1.1-4.1 months). Of the treated analysis set only 66 patients were included in the eligible analysis set since 6 patients were determined ineligible (4 because of absence of chemosensitivity to salvage therapy). The baseline characteristics of the 66 eligible patients are shown in Table 1.

TABLE 1

Baseline patient characteristics (eligible patients)

| Variable | Total N. (%)[a] |
|---|---|
| Number of patients | 66 |
| Age (years) (median, range) | 57 (19-80) |
| Race | |
| Asian/Oriental | 7 (11) |
| Black or African American | 3 (5) |
| Caucasian | 52 (79) |
| Hispanic | 4 (6) |
| Country | |
| Chile | 1 (1) |
| India | 3 (4) |
| Israel | 7 (11) |
| USA | 55 (83) |
| Gender | |
| Male | 43 (65) |
| Female | 23 (35) |
| Disease | |
| De novo DLBCL | 49 (74) |
| PMBCL | 4 (6) |
| Transformed indolent B-NHL | 13 (20) |
| IPI score at diagnosis | |
| 0-1 | 15 (23) |
| 2 | 11 (17) |
| 3 | 7 (11) |
| 4-5 | 7 (11) |
| Unknown | 26 (39) |
| Response to first-line therapy | |
| Complete remission | 45 (68) |
| Partial remission | 15 (23) |
| Stable or progressive disease | 5 (8) |
| Unknown | 1 (1) |
| Time from Diagnosis to ASCT | |
| Median in months (range) | 25 (8-186) |
| Characteristics at Relapse | |
| Stage[b] | |
| I | 6 (9) |
| II | 8 (12) |
| III | 9 (14) |
| IV | 18 (27) |
| Bulky[c] | 18 (27) |
| Extranodal involvement[d] | 18 (27) |
| Marrow involvement[e] | 29 (44) |
| IPI[f] | |
| 0-1 | 13 (20) |
| 2 | 7 (11) |
| 3 | 8 (12) |
| 4-5 | 2 (3) |
| Number of prior treatments | |
| 1 | 3 (5) |
| 2 | 47 (71) |
| 3 | 13 (20) |
| 4 | 3 (5) |
| Rituximab use | |
| With first line therapy | 56 (85) |
| With salvage therapy | 54 (82) |
| With conditioning | 10 (15) |
| Radiation Post-Transplantation | 5 (8) |
| Response to salvage therapy[g] | |
| PET negative | 31 (47) |
| PET positive | 24 (36) |
| PET not done | 11 (17) |
| Status before pidilizumab Treatment | |
| Complete remission | 31 (47) |
| Not in CR | 35 (53) |
| PET negative | 45 (68) |
| PET positive | 9 (18) |
| PET not done/missing | 12 (14) |

[a]Percentages may not add to 100 because of rounding. Denominator used were all patients including those with missing data.
[b]Data missing on 25 patients.
[c]Data missing on 9 patients.
[d]Data missing on 10 patients.
[e]Marrow biopsy was not performed on 3 patients; results were determined at time of diagnosis for primary refractory patients (SD + PD) or at last relapse prior to transplant for the others.
[f]Data missing on 36 patients.
[g]Patients with stable or progressive disease were assigned on retrospective review; they were not eligible for the study but are included in the treated analysis set.
DLBCL denotes diffuse large B-cell lymphoma;
PMBCL, primary mediastinal B-cell lymphoma;
B-NHL, B-cell non-Hodgkin lymphoma;
IPI, international prognostic index[29];
ASCT, autologous stem cell transplantation;
CR, complete remission.

The median age was 57 years (range, 19-80). The majority of patients had de novo DLBCL. The median time from diagnosis to ASCT was 25 months (range, 8-186). The median number of prior therapies (not counting ASCT) was 2 (24% of the patients had received more than 2). Most patients had received rituximab with first-line therapy (85%) and with salvage therapy (82%). Of the 66 eligible patients, 55 had a PET scan after salvage therapy (prior to AHSCT), among whom 24 patients (36%) had a positive scan. At the time of the first pidilizumab treatment, 47% of patients were in complete remission (CR) by conventional imaging, while 35 patients (53%) had persistent measurable disease. Among the 54 patients with a post-ASCT PET scan, 68% were in PET-CR (PET negative).

Correlative Studies

Blood samples collected from all treatment sites from patients treated at least once with pidilizumab were shipped, processed and analyzed by flow cytometry at 2 central laboratories using study-specific validated methodologies. The prospectively specified lymphocytes and myeloid cells consisting of 41 different subsets (Table 2) were evaluated for absolute CD marker population, percent of positive CD marker population of the analytical population, and MESF (Molecules of Equivalent Soluble Fluorochrome) by descriptive statistics. In the analysis, only absolute (as opposed to relative) numbers of lymphocyte subsets pre- and post-treatment were compared. In addition, MESF measurements were used to rule out the possibility that measured changes in the absolute numbers of a given immunophenotypic subset reflected change in surface expression of the chosen markers. The cellular and molecular changes following pidilizumab treatment were examined for their association with the primary clinical endpoint (progression-free survival rate at 16 months following pidilizumab administration).

TABLE 2

List of measured lymphocyte subsets

| Test | 1st marker | 2nd marker | 3rd marker | 4th marker | Purpose |
|---|---|---|---|---|---|
| 1 | CD3 | CD4 | HLA-DR | | T cell activation and CD4/CD8 ratio |
| 2 | CD3 | CD45RO | PD-1 | | PD-1 expression in effector/memory T cells |
| 3 | CD4 | CD45RO | CD62L | CCR7 | Characterization of central/effector memory T cells |
| 4 | CD8 | CD45RO | CD62L | CCR7 | Characterization of central/effector memory T cells |
| 5 | CD3 | CD56 | CD16 | | Activation of NK cells |
| 6 | CD3 | CD56 | CD107a | | Activation of NK cells |
| 7 | CD14 | B7-H1 | B7-DC | | Myelocytes/B7-DC/B7-H1 |
| 8 | CD20 | B7-H1 | PD-1 | | B cells/B7-H1/PD-1 |
| 9 | CD4 | B7-H1 | CD25 | | Regulatory T cells/B7-H1 |
| 10 | CD4 | CD8 | | | Double positive T cells |
| 11 | CD4 | CD62L | CD127 | | Characterization of memory T cells |
| 12 | CD8 | CD62L | CD127 | | Characterization of memory T cells |
| 13 | CD3 | CD4 | CD25 | FoxP3 | Characterization of regulatory T cells |

Statistical Considerations

Disease progression was determined based on Cheson's criteria (Cheson B D., et al. Revised Response Criteria for Malignant Lymphoma. J. Clin. Oncol 2007; 25 (5): 579-586. PMID: 17242396); in brief:
1. Appearance of any new lesion >1.5 cm in any axis (even if other lesions had decreased in size). In patients with no prior history of pulmonary lymphoma, new lung nodules identified by CT were mostly benign;
2. At least a 50% increase from nadir in the Sum Product of the Diameters (SPD) of any previously involved nodes, or in a single involved node, or the size of other lesions (e.g., splenic or hepatic nodules). To be considered progressive disease, a lymph node with a diameter of the short axis of <1.0 cm must have increased by ≥50% and to a size of 1.5×1.5 cm or >1.5 cm in the long axis;
3. At least a 50% increase in the longest diameter of any single previously identified node more than 1 cm in its short axis;
4. A PET scan was not required for determination of relapse or progression under this Protocol. However, in cases where only this test was available, lesions with PET positive that were negative in previous PET were considered as disease progression after confirmation with other modalities.

The primary endpoint of this study was the proportion of patients who did not relapse or die within 16 months of the 1st pidilizumab administration among all eligible patients who received at least 1 dose of pidilizumab. Secondary endpoints included safety and toxicity, and overall survival (OS), immunogenicity of pidilizumab, and immune subset analyses. OS was defined as the time from first pidilizumab administration to death, and PFS as the time from first pidilizumab administration to death, relapse or progression. OS and PFS were calculated using the Kaplan-Meier method. The expected 18-month PFS (from ASCT) in this population, based on historical experience, was estimated to be approximately 60% to 65% (Aksentijevich et al. Biol Blood Marrow Transplant 12:965-72, 2006).

The desired sample size was 64 eligible patients. Patients were eligible if they met all study inclusion and exclusion criteria and received at least 1 dose of pidilizumab. If more than 64 patients were treated, the minimum required 18-month PFS rate would have needed to be 0.69 to ensure a power of at least 87% at a 10% significance level. For patients with measurable disease at post-ASCT screening, response to pidilizumab treatment was assessed using standard criteria using the restaging schedule described above.

For measurements of immune subsets, absolute numbers of circulating lymphocytes of a given immunophenotype were compared before the first treatment and at 24 hours. 6, 12, 16 and 44 weeks afterwards. Changes in MESF were also measured in order to assess changes in surface expression of the relevant markers. Pre- and post-treatment values were compared using paired t-testing and trend testing for both the treated patients and the eligible patients. Outliers (with values from the mean of >3 SD) were excluded. We examined the correlation between the observed changes in absolute number of circulating lymphocyte/monocyte subsets or in receptor expression up to 16 weeks following treatment and patients' clinical outcome (using the primary endpoint of 16-month PFS rate). Those analyses were performed both in the treated and the eligible subject sets, using the two-sample non-parametric Wilcoxon-Mann-Whitney rank sum test for independent. Analysis of Covariance (ANCOVA) modeling was used to test the statistical significance of the difference in relative changes from baseline between patients who did or did not remain progression-free at 16 months, with adjustment for time on study. All reported p values are two-tailed, using a threshold for statistical significance of 0.05. The data was analyzed using the SAS @ version 9.1 (SAS Institute, Cary N.C.).

Analysis of Progression Free Survival and Overall Survival

Figure 2A:
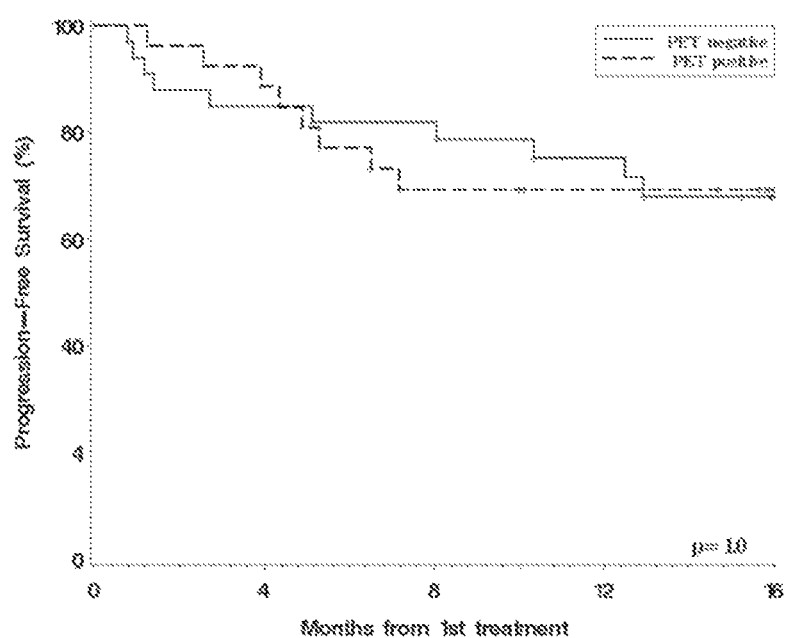
FIGS. 2A-B Show Kaplan-Meier models comparing progression-free survival (FIG. 2A) and overall survival (FIG. 2B) over time between two patient populations who were treated with pidilizumab following autologous stem cell transplantation (ASCT). One patient population was classified as positive by a pre-transplant PET imaging (continuous line, N=24). The other patient population was classified as negative by a pre-transplant PET imaging (segmented line, N=31).
Figure 2B:
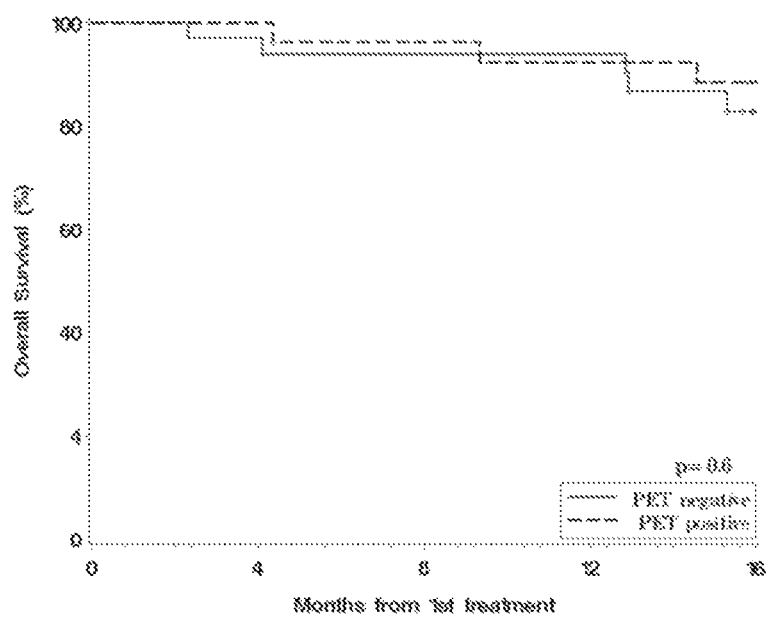

Of the 66 eligible patients, 24 patients had a positive PET-scan prior to ASCT, 31 had a negative PET-scan prior to ASCT and 11 did not have a post salvage PET scan. Among the 24 patients who remained PET-positive at the conclusion of salvage therapy (prior to ASCT), 16-month PFS from first pidilizumab treatment (18-month post-ASCT) was 70% (90%/CI: 51% to 82%; FIG. 2A). Among the 31 PET-negative patients prior to ASCT, 16-month PFS was 72% (90% CI: 56% to 84%); among the 11 patients who did not have a post salvage PET scan, 16-month PFS was 72% (90% CI: 42% to 88%). Among the 24 patients who remained PET-positive at the conclusion of salvage therapy (prior to ASCT), 16-month OS from first pidilizumab treatment was 91% (90% CI: 82% to 100%; FIG. 2B). Among the 31 patients who were PET-negative at the conclusion of salvage therapy (prior to ASCT), 16-month OS from first pidilizumab treatment was 82% (90% CI: 69% to 94%). (FIG. 2B). Among the 45 patients who were PET-negative following ASCT, 16-month OS from first pidilizumab treatment was 85% (90% CI: 76% to 94%).

The overall survival (OS) 18 months after ASCT in several historical patient cohorts with DLBCL and transformed follicular lymphoma ranges between 55% and 64%, approximately 20% lower than that obtained in the present study (Armand et al., Br J Haematol. 2013; Dickinson et al., Br J Haematol. 2010; amaras, et al., Swiss Med Wkly. 2013). While it is very hard to compare patient populations across cohorts, the evaluation shown in Table 3 clearly demonstrates that treatment with pidilizumab (pidilizumab) after transplant and for merely up to 3 times led to an increase in the survival of patients with a positive PET before ASCT.

TABLE 3

Comparison of Overall Survival in Patients with Positive PET Scan before transplant in the treated patients of the present study versus historical cohorts

| Study | No of Patient with positive PET pre-transplant | OS 18 months after transplant |
|---|---|---|
| The present study (Pidilizumab) | All treated patients N = 27 (20 DLBCL, 3 TFL, 4 other/unknown) | 88% (95% CI: 75, 100) |
| | DLBCL only N = 20 | 94% (95% CI: 84, 100) |
| Prognostic factors for patients with diffuse large B cell lymphoma and transformed indolent lymphoma undergoing autologous stem cell transplantation in the positron emission tomography era. Armand et al., Br J Haematol. 2013 | DLBCL patients N = 49 | ~64%[1] |
| | TFL patients N = 17 | ~58%[1] |
| Improved survival for relapsed diffuse large B cell lymphoma is predicted by a negative pre-transplant FDG-PET scan following salvage chemotherapy Dickinson et al., Br J Haematol 2010 | DLBCL patients N = 17 | ~55%[1] |
| Prognostic factors for survival in lymphoma patients after autologous stem cell transplantation | DLBCL patients (N = NA[2]) | ~58%[1] |
| Samaras, et al., Swiss Med Wkly. 2013 | All patients[3] (N = 39) | ~75%[1] |

Figure 1B:
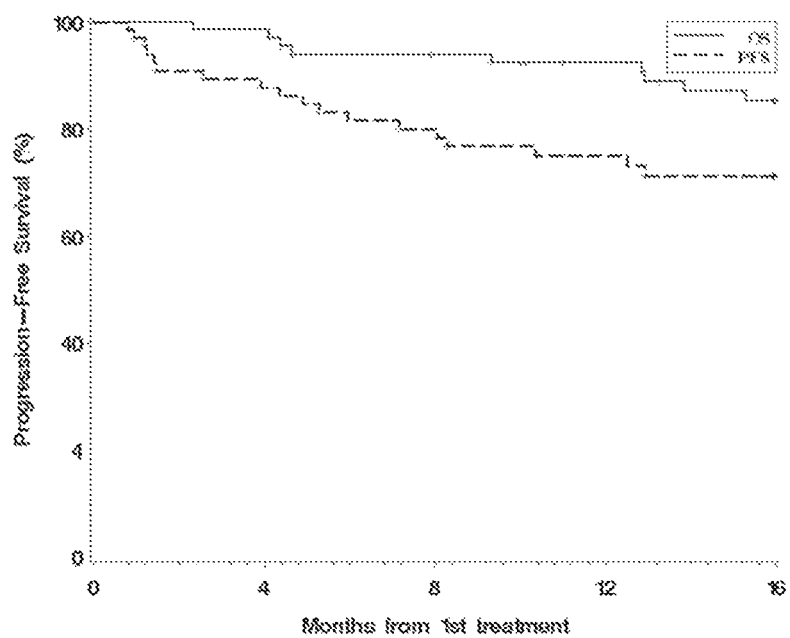

[1]Estimated from KM curves provided in the publications
[2]Number of DLBCL patients is not provided in the manuscript
[3]Composed of several diseases; Number of patients per each disease type is not available for this cohort Among the 66 eligible patients, 18 experienced disease progression or died before the 16-month time point. The 16-month PFS from first pidilizumab treatment (the primary end point) was 72% (90% CI: 60% to 82%; FIG. 1B). The study therefore met its primary end point. Nine patients died during the study period between 2.3 and 15.3 months; the cause of death was lymphoma in eight patients and disseminated herpes zoster in one patient. The 16-month OS for eligible patients was 85% (90% CI, 0.74 to 0.92; FIG. 1B). An intent-to-treat analysis was also performed for the 72 treated patients. As shown in FIG. 1A, the PFS at 16 months from first pidilizumab treatment in this cohort was 68% (90% CI: 59% to 77%), and OS was 84% (90% CI: 77% to 91%). Table 4 depicts clinical outcome data for the 72 treated patients. No significant difference was detected in the PFS or OS between treated patients when stratified by disease status assessed by CT scans after AHSCT, age, time to first relapse, time from diagnosis to AHSCT, or salvage regimen.

TABLE 4

Clinical Outcome - treated subgroup analysis

| Parameter | Subgroup | N | PFS | p | OS | p |
|---|---|---|---|---|---|---|
| Time from diagnosis to first relapse | ≤12 months | 14 | 0.57 | 0.38 | 0.71 | 0.07 |
| | >12 months | 43 | 0.70 | | 0.90 | |
| Time from diagnosis to transplant | ≤12 months | 12 | 0.67 | 0.82 | 0.67 | 0.06 |
| | >12 months | 60 | 0.70 | | 0.88 | |
| PET before transplant | Negative | 33 | 0.70 | 1.00 | 0.85 | 0.65 |
| | Positive | 27 | 0.70 | | 0.89 | |
| PET after transplant | Negative | 48 | 0.67 | 1.00 | 0.85 | 0.13 |
| | Positive | 12 | 0.67 | | 0.67 | |
| Disease status by CT scan after transplant | CR | 32 | 0.66 | 0.53 | 0.88 | 0.56 |
| | Non-CR | 40 | 0.73 | | 0.83 | |

TABLE 4-continued

Clinical Outcome - treated subgroup analysis

| Parameter | Subgroup | N | PFS | p | OS | p |
|---|---|---|---|---|---|---|
| Age | ≤55 years | 32 | 0.72 | 0.69 | 0.84 | 0.94 |
| | >55 years | 40 | 0.68 | | 0.85 | |
| Salvage regimen | ICE or R-ICE | 34 | 0.65 | 0.43 | 0.88 | 0.73 |
| | Other | 27 | 0.74 | | 0.85 | |

Analysis of Objective Response

Of the 66 eligible patients, 35 patients had measurable disease at screening post-ASCT and before the 1$^{st}$ dose of pidilizumab. Among these 35 patients, 15 (43%) achieved a complete remission (CR) after pidilizumab treatment, and 3 (9%) a partial remission (PR), for an overall response rate (ORR) of 51%. Of the 35 patients, 14 patients (40%) had stable disease (SD), while 3 (9%) had progressive disease (PD).

Twenty four of the 66 eligible patients had a positive PET scan prior to transplant. Fifteen of these patients had also measurable disease by CT scan after transplant. The ORR was 67% (10/115) including 9 (60%) patients in CR and 1 (7%) in PR. In addition, 5 (33%) of the patients were in SD and none in PD. The median time to response was 6.9 months (1.5-10.1) and the median duration of response has not been reached over the follow up period of 16 months after first administration of the antibody. The disease had not progressed in 11 (73%) of these 15 patients while 13 (87%) of them remained alive until the end of the study, 18 months after transplant.

Nine eligible patients with measurable disease by CT scan after transplant also had a positive PET at that time. The ORR was 33% (3/9) including 3 (33%) patients in CR. In addition, 4 (44%) of the patients were in SD and 2 (22%) in PD. The median time to response of these 3 subjects was 1.4 months (1.3-6.8) and response duration was 3.7, 5.9 and 14.4 months. Interestingly, 6 (67%) patients of this group of patients who are at the highest risk for disease progression after ASCT remained alive and without disease progression until the end of the study, 18 months after transplant. Table summarizes the objective response rate in DLBCL patients with measureable disease by their PET results.

TABLE 5

Objective Response Rate in DLBCL Patients with Measurable Disease after ASCT by their PET Results before or after Transplant - Eligible Patient Data Set

| Timing of PET | PET result | N | ORR N (%) | CR/CRu N (%) | PR N (%) | SD N (%) | PD N (%) |
|---|---|---|---|---|---|---|---|
| Before transplant | Negative | 15 | 5 (33) | 3 (20) | 2 (13) | 7 (47) | 3 (20) |
| | Positive | 15 | 10 (67) | 9 (60) | 1 (7) | 5 (33) | — |
| After transplant | Negative | 20 | 11 (55) | 9 (45) | 2 (10) | 8 (40) | 1 (5) |
| | Positive | 9 | 3 (33) | 3 (33) | — | 4 (44) | 2 (22) |

Immune Subset Analyses

Figure 3:
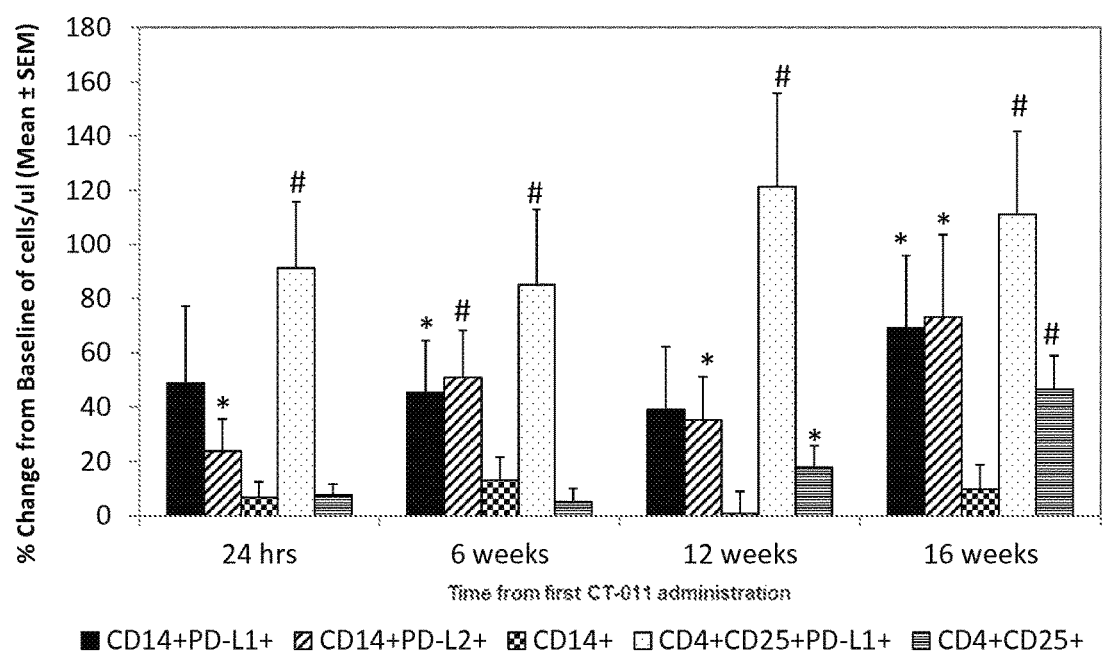
FIG. 3 is a bar-graph depicting the changes in the levels of several subsets of circulating lymphocytes following pidilizumab administration—PD-1 ligand baring monoxytes (CD14+B7-DC+ and CD14+B7-H1+), total CD14+ monocytes (CD14+), T-cells positive for B7-H1+ (CD4+CD25+B7-H+) and total CD4+CD25+ population (CD4+CD25+).
Figure 4:
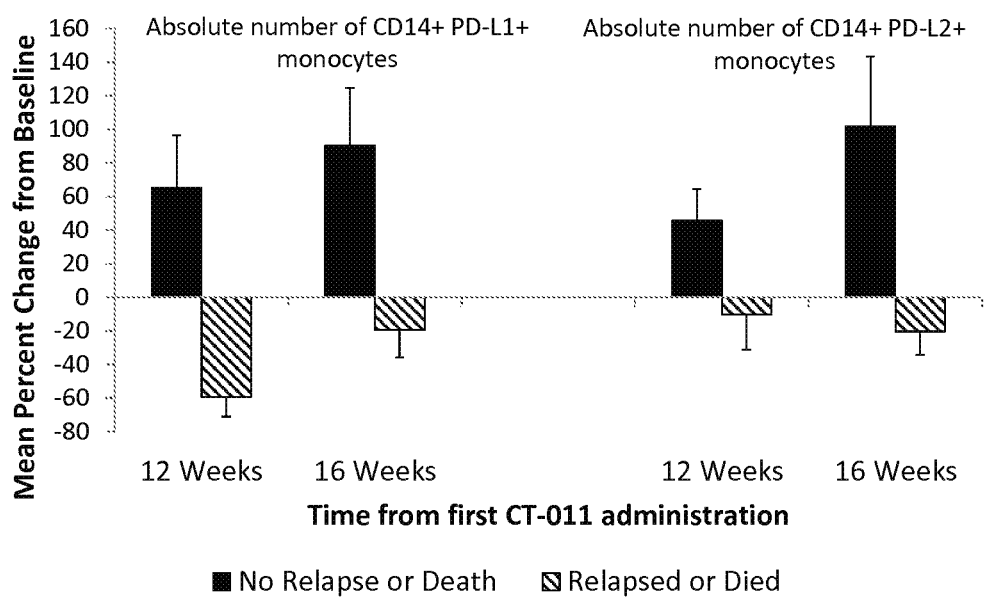
FIG. 4 is a bar graph depicting the correlation between clinical outcome and the changes in levels of circulating CD14+B7-H1+ cells (CD14+PD-L1+) and CD14+B7-DC+ cells (CD14+PD-L2+) in patients who underwent ASCT and received post-transplant administration of pidilizumab. Two patient populations are depicted: patients who remained progression-free until 18 months post-ASCT (No Relapse or Death) and patients who relapsed or dies by 18 months post-ASCT (Relapsed or Died). The graph depicts changes in the levels of the circulating lymphocytes 12 and 16 weeks following initial post-transplant administration of pidilizumab.

Samples for lymphocyte subset measurements were available for 66 of the 72 treated patients (92%). Treatment with pidilizumab resulted in an increase in the absolute number of both types of PD-1 ligand-bearing monocytes (CD14+B7-DC+ and CD14+B7-H1+ cells) and activated helper T cells (CD4+CD25+B7-H1+) (FIG. 3; (*) denotes $p \leq 0.05$, (#) denotes $p \leq 0.01$); significant changes in CD14+B7-DC+ cells and CD4+CD25+B7-H1+ cells were apparent within 24 hours of first dose and persisted at every time point until the last measurement. The increase in CD14+B7-H1+ was also apparent at all time points starting at 24 hours, although only some of the changes reached statistical significance. MESF analysis excluded the possibility that the above changes could be explained by up-regulation of surface markers. Among the eligible patients, there appeared to be a correlation between the changes in circulating CD14+B7-H1+ cells and clinical outcome (FIG. 4): at 12 weeks post-treatment, there was an increase (from baseline) of 65% in patients who remained progression-free until 18 months post-ASCT, compared to a decrease of 59% in those who did not ($p=0.0^{34}$). The trend remained at 16 weeks (with a mean increase of 90% in patients who remained progression free compared to a mean decrease of 20% for those who did not, $p=0.089$). Patients who remained progression free throughout the study demonstrated a mean increase in CD14+B7-DC+ cells of 46% and 102% at 12 and 16 weeks after first pidilizumab administration, respectively, while patients who relapsed or died during this period demonstrated mean decreases of 10% and 20% in these cells at the same time points. These differences were not statistically significant.

Figure 5:
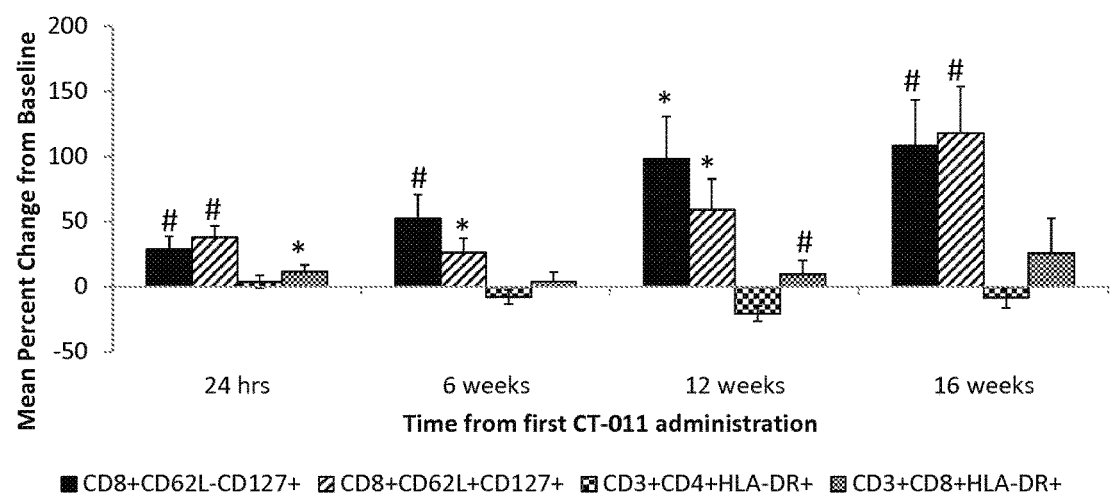
FIG. 5 is a bar-graph depicting the changes in the levels of several subsets of peripheral and central memory CD8 T cells following pidilizumab administration.

We also found a significant increase in the absolute number of circulating CD8+ peripheral (CD8+CD62L-CD127+) and central (CD8+CD62L+CD127+) memory T cells, apparent 24 hours after the first dose of pidilizumab and persisting at all time points (FIG. 5; (*) denotes $p \leq 0.05$. (#) denotes $p \leq 0.01$). Among the 40 subjects who remained progression-free at 18 months after ASCT, there was a mean increase of 9% in the absolute numbers of CD8+CD62L-CD127+ 24 hours after first pidilizumab administration, compared with a 68% mean increase among the 20 patients who progressed or died by 16 months ($p=0.006$).

Figure 6:
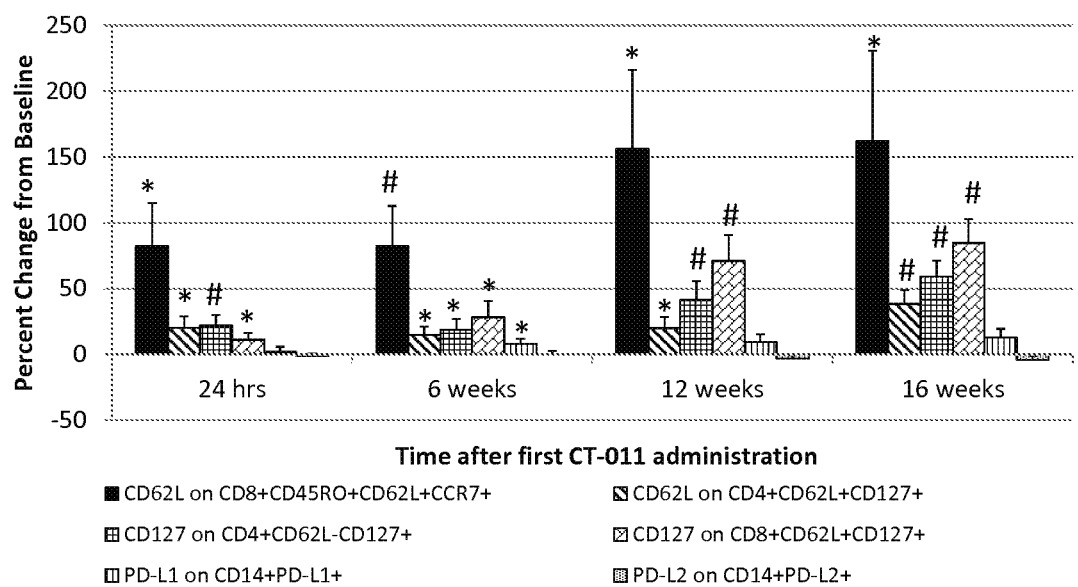
FIG. 6 is a bar-graph depicting the changes in the expression level of selected cell surface receptors on T cells and monocytes after pidilizumab administration.

Furthermore, there was a significant increase in the cell surface expression of CD62L, a lymph node homing receptor, on CD8+CD45RO+CD62L+CCR7+ cells, apparent within 24 hours after first pidilizumab administration, with a further increase apparent by 12 weeks. Significant increases in the expression of CD62L were also found for CD4+CD127+CD62L+ and CD8+CD127+CD62L+ cells (FIG. 6; (*) denotes $p \leq 0.05$, (#) denotes $p \leq 0.01$). In addition, a moderate yet continued increase was noted in the expression of the IL-7α receptor (CD127), pivotal for the maturation and survival of memory T cells, on CD4+CD62L-CD127+, CD4+CD62L+CD127+ and CD8+CD62L+CD127+ cells. This increase in receptor expression was demonstrable 24 hours after first pidilizumab administration and persisted at later time points (FIG. 6).

Safety and Toxicity

Of the 72 patients who received at least 1 dose of pidilizumab, 60 completed all 3 cycles of treatment. One patient died of disseminated herpes zoster 10 months after the $3^{rd}$ dose of pidilizumab; this event was considered unrelated to study treatment. Reasons for withdrawal among the other 31 patients were disease progression (21), loss to follow-up (3), investigator decision (3), withdrawal of consent (2), protocol violation (1), and adverse event (1). Adverse events (AEs) are detailed in Table 6. Data is shown as number of patients with a given AE (number of events are shown in parentheses). Only AEs occurring in at least 2 patients (≥2% of total events) are shown.

TABLE 6

Most Frequent Adverse Events

| | Number of patients (Number of events) Severity Grade | | | | | |
|---|---|---|---|---|---|---|
| Event | All | 1 | 2 | 3 | 4 | 5 |
| All | 69 (613) | 65 (392) | 49 (145) | 30 (60) | 9 (14) | 1 (1) |
| Neutropenia | 19 (25) | 3 (3) | 7 (7) | 9 (10) | 5 (5) | — |
| Fatigue | 18 (21) | 16 (19) | 2 (2) | — | — | — |
| Upper respiratory tract infection | 14 (15) | 9 (10) | 5 (5) | — | — | — |
| Diarrhea | 12 (19) | 10 (14) | 4 (5) | — | — | — |
| Cough | 12 (14) | 11 (13) | 1 (1) | — | — | — |
| Thrombocytopenia | 10 (15) | 5 (6) | — | 4 (5) | 2 (4) | — |
| Hyperglycemia | 9 (12) | 8 (10) | 2 (2) | — | — | — |
| White blood cell count decrease | 9 (12) | 6 (8) | 3 (3) | 1 (1) | — | — |

A total of 613 AEs were reported in 69 (96%) of patients, among which 135 AEs (experienced by 37 patients (51%)) were related to study treatment. Twenty-three patients (32%) experienced at least 1 serious AE (SAE) and 3 patients (4%) experienced a related SAE. One patient was prematurely withdrawn from the study due to an AE that occurred after the last administration of pidilizumab at week 12. Among the 613 AEs, 64% were mild, 24% moderate, 10% severe, and 2% life threatening.

The most frequently reported AEs (comprising at least 2% of events) are listed in Table 6. The most frequently reported grade 3-4 AEs were neutropenia (19% of patients) and thrombocytopenia (8% of patients). There was no evidence of significant autoimmune toxicity, no infusion reactions, and no treatment-related mortality.

In the present trial, we show that the pidilizumab antibody can be safely given to patients with NHL (e.g., DLBCL) after autologous transplantation (e.g., ASCT). Most adverse events were grade 1 or 2, with rare grade 3/4 cytopenias. Notably there was no infusion toxicity and no evidence of significant autoimmune toxicity (in contrast to the clinical experience so far with CTLA-4 blockade (Di Giacomo A M, et al. Semin Oncol 37:499-507, 2010)). Treatment with pidilizumab was associated with an apparent complete remission (CR) rate of 43% and overall response rate of 51% among patients with measurable disease post-transplant, which suggests direct anti-tumor activity. Moreover, with a 16-month progression-free survival of 72%, the study met its pre-specified primary endpoint, demonstrating that pidilizumab treatment after ASCT has promising activity against NHL, as further supported by the robust 18-month OS of 84%. There appears to be a particularly beneficial effect in patients who are still PET-positive after salvage therapy.

Concomitant with the improvement in the outcome of first-line therapy from the use of rituximab, it has become clear that the prognosis of patients who relapse after rituximab-containing therapy is worse than it was in the pre-rituximab era, even with modern salvage and ASCT techniques (Gisselbrecht C, et al: J Clin Oncol 28:4184-90, 2010). This appears to stem from lower response and complete remission rates with salvage therapy after rituximab failure, which in turn worsens the outcome of ASCT (or preclude patients from proceeding to ASCT in the case of chemo-refractory disease). New therapies to increase the efficacy of salvage therapy, and to increase the success rate of ASCT in patients without a PET negative result before transplantation, are therefore much needed.

Recently, Armand et al. reported the outcomes of 105 patients with DLBCL who underwent transplantation in the last decade. Among this cohort, the outcome of 46 patients who were chemosensitive but PET positive after salvage was examined. In this group, the 18-month post-AHSCT PFS was 0.52 (90% CI, 0.39 to 0.63). It has been well recognized that a positive pre-transplant metabolic imaging, including for example a PET scan positive and a GA scan positive result, is predictive of poor clinical outcome in terms of OS and PFS in lymphoma patients following ASCT (Puolou et al. 2010 ibid.).

The inventors have surprisingly found that among all treated patients with different non-Hodgkin's lymphomas who received pidilizumab monoclonal antibody following ASCT, the 16-month PFS in patients who remained PET-positive at the conclusion of salvage therapy (positive pre-transplant imaging) was 70%, and identical to that of the patients who achieved a pre-transplant PET-negative remission (p=1.0; all treated patients). In addition, the inventors surprisingly found that the Overall Survival (OS) rate at 16 months after first pidilizumab treatment was similar between pre-transplant PET positive and pre-transplant PET negative patients (82% for PET-negative versus 91% for PET-positive patients, p=0.65). These findings are unexpected in light of the results of the recently completed CORAL study in which the differences between subjects who were PET positive and negative prior to transplant have been assessed (Trneny, M., et al.; Independent Predictive Value of PET-CT Pre Transplant in Relapsed and Refractory Patients with CD20 Diffuse Large B-Cell Lymphoma (DLBCL) Included in the CORAL Study; Program and abstracts of the 51st American Society of Hematology Annual Meeting and Exposition; Dec. 5-8, 2009; New Orleans, La. Abstract 881). The analyses presented in this abstract indicate that the 3 year PFS for DLBCL subjects who were PET negative after salvage therapy was 43% and significantly higher (p<0.0001) that that of patients with post-salvage positive PFS which was 28%. The 3 year OS was significantly (p<0.007) higher for subjects who were PET negative (66%) after salvage compared with subjects who were PET positive (49%) post salvage.

These unexpected results suggest that BAT monoclonal antibody (i.e., pidilizumab) can be used in the high-risk subset of non-Hodgkin's lymphoma patients undergoing ASCT with a positive pre-transplant metabolic imaging. It would be appreciated by the person skilled in the art that the same useful effect would be expected in patients undergoing other types of stem cell transplantation, which similarly involve eradication of the BM cells and replenishing with stem cells. It would be appreciated by the person skilled in the art that the same useful effect would be expected in patients suffering from other tumor types and specifically Hodgkin's disease, which undergo conditioning treatments and stem cell transplantation. It would be expected that pidilizumab administration should have beneficial effects in inducing anti-tumor activity in immune cells during bone marrow replenishing.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. An immunotherapy method of treating non-Hodgkin's lymphoma in a human subject suffering from non-Hodgkin's lymphoma and requiring stem cell transplantation, comprising the steps of: performing a pre-transplant metabolic imaging; classifying the subject as positive by the metabolic imaging; administering following stem cell transplantation to the subject a therapeutically effective amount of a pidilizumab monoclonal antibody or a fragment thereof comprising a light chain variable region comprising CDRs having the sequences SEQ. ID NO. 13, SEQ. ID NO. 14 and SEQ. ID NO. 15 and a heavy chain variable region comprising CDRs having the sequences: SEQ. ID NO. 16, SEQ. ID NO. 17 and SEQ. ID NO. 18, so as to thereby treat non-Hodgkin's lymphoma or extend progression-free or overall survival in the subject, wherein said subject is classified as positive by a pre-transplant metabolic imaging; and wherein the first administration of the antibody is within 2-12 weeks after the stem cell transplantation.

2. The method of claim 1, wherein said fragment of pidilizumab monoclonal antibody is selected from the group consisting of: Fab, Fab', F(ab')$_2$, Fv; single-chain antibody molecules and multi-specific antibodies formed from antibody fragments.

3. The method of claim 1, wherein the pidilizumab monoclonal antibody comprises a light chain variable region as set forth in SEQ ID NO: 22 (BATRκ$_D$) and a heavy chain variable region as set forth in SEQ ID NO: 25 (BATRH$_C$).

4. The method of claim 1, wherein the pidilizumab monoclonal antibody comprises a light chain variable region selected from the group consisting of: BATRκa (SEQ. ID NO. 19), BATRκb (SEQ. ID NO. 20), BATRκc (SEQ. ID NO. 21), BATRκd (SEQ. ID NO. 22), and the heavy chain variable region is selected from the group consisting of: BATRH$_A$ (SEQ. ID NO. 23), BATRH$_B$ (SEQ. ID NO. 24), BATRH$_C$ (SEQ. ID NO. 25), BATRH$_D$ (SEQ. ID NO. 26) and BATRH$_E$ (SEQ. ID NO. 27).

5. The method of claim 1, wherein the pidilizumab monoclonal antibody comprises a variable region selected from the group consisting of: BATRHA/BATRκa (SEQ. ID NO. 23/SEQ. ID NO. 19), BATRH$_B$/BATRκa (SEQ. ID NO. 24/SEQ. ID NO. 19), BATRH$_B$/BATRκb (SEQ. ID NO. 24/SEQ. ID NO. 20), BATRH$_C$/BATRκb (SEQ. ID NO. 25/SEQ. ID NO. 20), BATRH$_B$/BATRκd (SEQ. ID NO. 24/SEQ. ID NO. 22), and BATRH$_C$/BATRκd (SEQ. ID NO. 25/SEQ. ID NO. 22).

6. The method of claim 1, wherein the stem cell transplantation is autologous stem cell transplantation.

7. The method of claim 1, wherein the stem cell transplantation is allogeneic stem cell transplantation.

8. The method of claim 1, wherein stem cells for said stem cell transplantation are derived from umbilical cord.

9. The method of claim 1, wherein the metabolic imaging is selected from PET imaging and Ga imaging.

10. The method of claim 1, wherein the non-Hodgkin's lymphoma is selected from the group consisting of: Burkitt lymphoma, chronic lymphocytic leukemia/small lymphocytic lymphoma, diffuse large B-cell lymphoma, follicular lymphoma, immunoblastic large cell lymphoma, precursor B-lymphoblastic lymphoma, mantle cell lymphoma, mycosis fungoides, anaplastic large cell lymphoma, precursor T-lymphoblastic lymphoma, AIDS-Related Lymphomas, Angioimmunoblastic Lymphoma, Blastic NK-Cell Lymphoma, Cutaneous T-Cell Lymphoma, Enteropathy-Type T-Cell Lymphoma, Hepatosplenic Gamma-Delta T-Cell Lymphoma, Lymphoblastic Lymphoma, Marginal Zone Lymphoma, Nasal T-Cell Lymphoma, Pediatric Lymphoma, Peripheral T-Cell Lymphomas, Primary Central Nervous System Lymphoma, T-Cell Leukemias, Transformed Lymphomas, Treatment-Related T-Cell Lymphomas and Waldenstrom's Macroglobulinemia.

11. The method of claim 1, wherein the non-Hodgkin's lymphoma is selected from the group consisting of: diffuse large B cell lymphoma, primary mediastinal B-cell lymphoma and transformed indolent B cell non-Hodgkin's lymphoma.

12. The method of claim 1, wherein the pidilizumab monoclonal antibody or fragment thereof is administered via intravenous infusion.

13. The method of claim 1, wherein the pidilizumab monoclonal antibody is administered periodically.

14. The method of claim 13, wherein the antibody is periodically administered according to an administration regime selected from the group consisting of: between 1-30 times within a period of 24 months following the stem cell transplantation; administration between 1-30 times within a period of 18 months following the stem cell transplantation; between 1-12 times within a period of 18 months following the stem cell transplantation; at least 3 times within a period of 18 months following the stem cell transplantation; 3 times within a period of 18 weeks; 3 times within a period of 12 weeks; 6 times within a period of 24 weeks; 12 times within a period of 24 weeks; 12 times within a period of 48 weeks; and 27 times within a period of 54 weeks.

15. The method of claim 13, wherein the periodic administration is every two-six weeks.

16. The method of claim 1, wherein the therapeutically effective amount is 1-6 mg/kg.

17. The method of claim 1, wherein the subject is diagnosed as having a measurable disease after the stem cell therapy.

18. The method of claim 1, further comprising administering at least one additional anti-cancer agent selected from the group consisting of: an anti-metabolic agent, an anti-angiogenic agent, a cytotoxic agent, anti-tumor therapeutic antibodies and cell based therapies and combinations thereof.

19. The method of claim 18, wherein the anti-tumor therapeutic antibody is Rituximab.

20. The method of claim 18, wherein said therapeutically effective amount of pidilizumab monoclonal antibody and said at least one therapeutic agent are administered together or sequentially.

21. The method of claim 1, wherein said treating or enhancing survival is associated with an increase in the level of circulating lymphocytes selected from the group consisting of: CD14+PD-L1+, CD14+PD-L2+ and a combination thereof.

22. The method of claim 1, wherein a first administration of the antibody is within 4-12 weeks after the stem cell transplantation.

23. The method of claim 22, wherein second and third administrations of the antibody are carried out in 6-weeks intervals.

* * * * *

UNITED STATES PATENT AND TRADEMARK OFFICE
CERTIFICATE OF CORRECTION

PATENT NO.       : 9,580,504 B1
APPLICATION NO.  : 14/536343
DATED            : February 28, 2017
INVENTOR(S)      : Rotem-Yehudar et al.

Page 1 of 1

It is certified that error appears in the above-identified patent and that said Letters Patent is hereby corrected as shown below:

On the Title Page
Item (56) References Cited, OTHER PUBLICATIONS:
"Bendig" reference: delete "Gafting" and insert -- Grafting --.
"Bruccoleri and Karplus" reference: delete "Predicton" and insert -- Prediction --.
"Clark" reference: delete "'Emperors's" and insert -- 'Emperor's --.
"Dickson" reference: delete "Impoved survival for ralapsed" and insert -- Improved survival for relapsed --.
"Fang et al." reference: delete "111b" and insert -- IIIb --.
"Foote and Winter" reference: delete "famework esidues" and insert -- framework residues --; and delete "hyperarable" and insert -- hypervariable --.
"Junghans et al." reference: delete "Ant-Ta-H" and insert -- Anti-Tac-H --; and delete "intereukin 2 recepor" and insert -- interleukin receptor --.
"Kettleborough et al." reference: delete "Optimizton of primes" and insert -- Optimization of primers --; and delete "immunogobulin" and insert -- immunoglobulin --.
"Pardoll and Topalian" reference: delete "Tthe ole of CD4+ T cel" and insert -- The role of CD4+ T Cell --; and after "antitumor immunity" insert -- . --.
"Quaglino et al." reference: delete "progession" and insert -- progression --.
"Queen et al." reference: delete "intereukin" and insert -- interleukin --.
"Raiter et al." (1999) reference: delete "Activaton" and insert -- Activation --; and delete "comparson" and insert -- comparison --.
"Raiter et al." (2000) reference: delete "celluar" and insert -- cellular --; and delete "stimuaton" and insert -- stimulation --.
"Sehn et al." reference: delete "Chop" and insert -- CHOP --.
"Tramontano et al." reference: delete "positon and conformaton" and insert -- position and conformation --.

Signed and Sealed this
Eleventh Day of April, 2017

Michelle K. Lee
*Director of the United States Patent and Trademark Office*

SEQUENCE LISTING

```
<160> NUMBER OF SEQ ID NOS: 29

<210> SEQ ID NO 1
<211> LENGTH: 408
<212> TYPE: DNA
<213> ORGANISM: Artificial Sequence
<220> FEATURE:
<223> OTHER INFORMATION: Heavy chain variable region of the BAT
      monoclonal antibody

<400> SEQUENCE: 1
atggcttggg tgtggacctt gctattcctg atggcagctg cccaaagtat ccaagcacag      60
atccagttgg tgcagtctgg acctgagttg aagaagcctg gagagacagt caagatctcc     120
tgcaaggctt ctggatatac tttcacaaac tatggaatga ctgggtgaa gcaggctcca      180 ggaaagggtt taaagtggat gggctggata aacaccgaca gtggagagtc aacatatgct     240
gaagagttca agggacggtt tgccttctct ttggaaacct ctgccaacac tgcctatttg     300
cagatcaaca acctcaacaa tgaggacacg gctacatatt tctgtgtgag agtcggctac     360
gatgctttgg actactgggg tcaaggaacc tcagtcaccg tctcctca                  408

<210> SEQ ID NO 2
<211> LENGTH: 408
<212> TYPE: DNA
<213> ORGANISM: Artificial Sequence
<220> FEATURE:
<223> OTHER INFORMATION: Heavy chain variable region of the BAT
      monoclonal antibody

<400> SEQUENCE: 2
atggcttggg tgtggacctt gctattcctg atggcagctg cccaaagtat ccaagcacag      60
atccagttgg tgcagtctgg acctgagttg aagaagcctg gagagacagt caagatctcc     120
tgcaaggctt ctggatatac tttcacaaac tatggaatga ctgggtgaa gcaggctcca      180 ggaaagggtt taaagtggat gggctggata aacaccgaca gtggagagtc aacatatgct     240
gaagagttca agggacggtt tgccttctct ttggaaacct ctgccaacac tgcctatttg     300
cagatcaaca acctcaacaa tgaggacacg gctacatatt tctgtgtgag agtcggctac     360
gatgctttgg actactgggg tcaaggaacc tcagtcaccg tctcctca                  408

<210> SEQ ID NO 3
<211> LENGTH: 384
<212> TYPE: DNA
<213> ORGANISM: Artificial Sequence
<220> FEATURE:
<223> OTHER INFORMATION: Light chain variable region of the BAT
      monoclonal antibody

<400> SEQUENCE: 3
atggatttac aggtgcagat tatcagcttc ctgctaatca gtgcctcagt cataatgtcc      60
agaggacaaa ttgttctcac ccagtctcca gcaatcatgt ctgcatctcc aggggagaag     120
```

-continued

```
gtcaccataa cctgcagtgc caggtcaagt gtaagttaca tgcactggtt ccagcagaag    180
ccaggcactt ctcccaaact ctggatttat aggacatcca acctggcttc tggagtccct    240
gctcgcttca gtggcagtgg atctgggacc tcttactgtc tcacaatcag ccgaatggag    300
gctgaagatg ctgccactta ttactgccag caaaggagta gtttcccact cacgttcggc    360
tcggggacaa agttggaaat aaaa                                           384
```

<210> SEQ ID NO 4
<211> LENGTH: 384
<212> TYPE: DNA
<213> ORGANISM: Artificial Sequence
<220> FEATURE:
<223> OTHER INFORMATION: Light chain variable region of the BAT
      monoclonal antibody

<400> SEQUENCE: 4

```
atggatttac aggtgcagat tatcagcttc ctgctaatca gtgcctcagt cataatgtcc     60
agaggacaaa ttgttctcac ccagtctcca gcaatcatgt ctgcatctcc aggggagaag    120
gtcaccataa cctgcagtgc caggtcaagt gtaagttaca tgcactggtt ccagcagaag    180
ccaggcactt ctcccaaact ctggatttat aggacatcca acctggcttc tggagtccct    240
gctcgcttca gtggcagtgg atctgggacc tcttactgtc tcacaatcag ccgaatggag    300
gctgaagatg ctgccactta ttactgccag caaaggagta gtttcccact cacgttcggc    360
tcggggacaa agttggaaat aaaa                                           384
```

<210> SEQ ID NO 5
<211> LENGTH: 23
<212> TYPE: PRT
<213> ORGANISM: Artificial Sequence
<220> FEATURE:
<223> OTHER INFORMATION: Frame region of the light chain variable region
      of the human TEL9 antibody

<400> SEQUENCE: 5

```
Glu Ile Val Leu Thr Gln Ser Pro Ser Ser Leu Ser Ala Ser Val Gly
1               5                   10                  15

Asp Arg Val Thr Ile Thr Cys
            20
```

<210> SEQ ID NO 6
<211> LENGTH: 15
<212> TYPE: PRT
<213> ORGANISM: Artificial Sequence
<220> FEATURE:
<221> NAME/KEY: MOD_RES
<222> LOCATION: (2)..(2)
<223> OTHER INFORMATION: Phe or Tyr
<220> FEATURE:
<221> NAME/KEY: MOD_RES
<222> LOCATION: (13)..(13)
<223> OTHER INFORMATION: Trp or Leu
<220> FEATURE:
<223> OTHER INFORMATION: Frame region of the light chain variable region
      of the human TEL9 antibody

<400> SEQUENCE: 6

```
Trp Xaa Gln Gln Lys Pro Gly Lys Ala Pro Lys Leu Xaa Ile Tyr
1               5                   10                  15
```

<210> SEQ ID NO 7
<211> LENGTH: 32
<212> TYPE: PRT

```
<213> ORGANISM: Artificial Sequence
<220> FEATURE:
<221> NAME/KEY: MOD_RES
<222> LOCATION: (14)..(14)
<223> OTHER INFORMATION: Asp or Ser
<220> FEATURE:
<221> NAME/KEY: MOD_RES
<222> LOCATION: (15)..(15)
<223> OTHER INFORMATION: Phe or Tyr
<220> FEATURE:
<221> NAME/KEY: MOD_RES
<222> LOCATION: (16)..(16)
<223> OTHER INFORMATION: Cys or Thr
<220> FEATURE:
<223> OTHER INFORMATION: Frame region of the light chain variable region
      of the human TEL9 antibody

<400> SEQUENCE: 7

Gly Val Pro Ser Arg Phe Ser Gly Ser Gly Ser Gly Thr Xaa Xaa Xaa
1               5                   10                  15

Leu Thr Ile Asn Ser Leu Gln Pro Glu Asp Phe Ala Thr Tyr Tyr Cys
            20                  25                  30

<210> SEQ ID NO 8
<211> LENGTH: 10
<212> TYPE: PRT
<213> ORGANISM: Artificial Sequence
<220> FEATURE:
<223> OTHER INFORMATION: Frame region of the light chain variable region
      of the human TEL9 antibody

<400> SEQUENCE: 8

Phe Gly Gly Gly Thr Lys Leu Glu Ile Lys
1               5                   10

<210> SEQ ID NO 9
<211> LENGTH: 30
<212> TYPE: PRT
<213> ORGANISM: Artificial Sequence
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (28)..(28)
<223> OTHER INFORMATION: Thr or Ser
<220> FEATURE:
<221> NAME/KEY: MOD_RES
<222> LOCATION: (30)..(30)
<223> OTHER INFORMATION: Thr or Ser
<220> FEATURE:
<223> OTHER INFORMATION: Frame region of the heavy chain variable region
      of the human hsighv 1295 antibody

<400> SEQUENCE: 9

Gln Xaa Gln Leu Val Gln Ser Gly Ser Glu Leu Lys Lys Pro Gly Ala
1               5                   10                  15

Ser Val Lys Ile Ser Cys Lys Ala Ser Gly Tyr Xaa Phe Xaa
            20                  25                  30

<210> SEQ ID NO 10
<211> LENGTH: 14
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
```

```
<222> LOCATION: (11)..(11)
<223> OTHER INFORMATION: Gln or Lys
<220> FEATURE:
<223> OTHER INFORMATION: Frame region of the heavy chain variable region
      of the human hsighv 1295 antibody

<400> SEQUENCE: 10

Trp Val Xaa Gln Ala Pro Gly Gln Gly Leu Xaa Trp Met Gly
1               5                   10

<210> SEQ ID NO 11
<211> LENGTH: 32
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: Val or Ala
<220> FEATURE:
<221> NAME/KEY: MOD_RES
<222> LOCATION: (11)..(11)
<223> OTHER INFORMATION: Asn or Ser
<220> FEATURE:
<221> NAME/KEY: MOD_RES
<222> LOCATION: (21)..(21)
<223> OTHER INFORMATION: Asn or Thr
<220> FEATURE:
<221> NAME/KEY: MOD_RES
<222> LOCATION: (31)..(31)
<223> OTHER INFORMATION: Val or Ala
<220> FEATURE:
<221> NAME/KEY: MOD_RES
<222> LOCATION: (32)..(32)
<223> OTHER INFORMATION: Arg or Lys
<220> FEATURE:
<223> OTHER INFORMATION: Frame region of the heavy chain variable region
      of the human hsighv 1295 antibody

<400> SEQUENCE: 11

Arg Phe Xaa Phe Ser Leu Asp Thr Ser Val Xaa Thr Ala Tyr Leu Gln
1               5                   10                  15

Ile Thr Ser Leu Xaa Ala Glu Asp Thr Gly Met Tyr Phe Cys Xaa Xaa
            20                  25                  30

<210> SEQ ID NO 12
<211> LENGTH: 11
<212> TYPE: PRT
<213> ORGANISM: Artificial Sequence
<220> FEATURE:
<223> OTHER INFORMATION: Frame region of the heavy chain variable region
      of the human hsighv 1295 antibody

<400> SEQUENCE: 12

Trp Gly Gln Gly Thr Leu Val Thr Val Ser Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Light chain variable region comprising CDRs of
      the BAT monoclonal antibody

<400> SEQUENCE: 13

Ser Ala Arg Ser Ser Val Ser Tyr Met His
1               5                   10

<210> SEQ ID NO 14
<211> LENGTH: 7
```

```
<212> TYPE: PRT
<213> ORGANISM: Artificial Sequence
<220> FEATURE:
<223> OTHER INFORMATION: Light chain variable region comprising CDRs of
      the BAT monoclonal antibody

<400> SEQUENCE: 14

Arg Thr Ser Asn Leu Ala Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Light chain variable region comprising CDRs of
      the BAT monoclonal antibody

<400> SEQUENCE: 15

Gln Gln Arg Ser Ser Phe Pro Leu Thr
1               5

<210> SEQ ID NO 16
<211> LENGTH: 5
<212> TYPE: PRT
<213> ORGANISM: Artificial Sequence
<220> FEATURE:
<223> OTHER INFORMATION: Heavy chain variable region comprising CDRs of
      the BAT monoclonal antibody

<400> SEQUENCE: 16

Asn Tyr Gly Met Asn
1               5

<210> SEQ ID NO 17
<211> LENGTH: 17
<212> TYPE: PRT
<213> ORGANISM: Artificial Sequence
<220> FEATURE:
<223> OTHER INFORMATION: Heavy chain variable region comprising CDRs of
      the BAT monoclonal antibody

<400> SEQUENCE: 17

Trp Ile Asn Thr Asp Ser Gly Glu Ser Thr Tyr Ala Glu Glu Phe Lys
1               5                   10                  15
Gly

<210> SEQ ID NO 18
<211> LENGTH: 8
<212> TYPE: PRT
<213> ORGANISM: Artificial Sequence
<220> FEATURE:
<223> OTHER INFORMATION: Heavy chain variable region comprising CDRs of
      the BAT monoclonal antibody

<400> SEQUENCE: 18

Val Gly Tyr Asp Ala Leu Asp Tyr
1               5

<210> SEQ ID NO 19
<211> LENGTH: 106
<212> TYPE: PRT
<213> ORGANISM: Artificial Sequence
<220> FEATURE:
<223> OTHER INFORMATION: Light chain variable region of humanized BAT
      monoclonal antibody BATRKa

<400> SEQUENCE: 19
```

```
Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105
```

<210> SEQ ID NO 20
<211> LENGTH: 106
<212> TYPE: PRT
<213> ORGANISM: Artificial Sequence
<220> FEATURE:
<223> OTHER INFORMATION: Light chain variable region of humanized BAT
      monoclonal antibody BATRKb

<400> SEQUENCE: 20

```
Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105
```

<210> SEQ ID NO 21
<211> LENGTH: 106
<212> TYPE: PRT
<213> ORGANISM: Artificial Sequence
<220> FEATURE:
<223> OTHER INFORMATION: Light chain variable region of humanized BAT
      monoclonal antibody BATRKc

<400> SEQUENCE: 21

```
Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Cys Leu Thr Ile Asn Ser Leu Gln Pro Glu
65                  70                  75                  80
```

```
Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: Light chain variable region of humanized BAT
      monoclonal antibody BATRKd

<400> SEQUENCE: 22

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
                20                  25                  30

His Trp Phe Gln Gln Lys Pro Gly Lys Ala Pro Lys Leu Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 23
<211> LENGTH: 117
<212> TYPE: PRT
<213> ORGANISM: Artificial Sequence
<220> FEATURE:
<223> OTHER INFORMATION: Heavy chain variable region of humanized BAT
      monoclonal antibody BATRHA

<400> SEQUENCE: 23

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Ser Asn Tyr
                20                  25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
        50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Val Gly Tyr Asp Ala Leu Asp Tyr Trp Gly Gln Gly Thr Leu
            100                 105                 110

Val Thr Val Ser Ser
        115

<210> SEQ ID NO 24
<211> LENGTH: 117
<212> TYPE: PRT
<213> ORGANISM: Artificial Sequence
```

```
<220> FEATURE:
<223> OTHER INFORMATION: Heavy chain variable region of humanized BAT
      monoclonal antibody BATRHB

<400> SEQUENCE: 24

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Val Gly Tyr Asp Ala Leu Asp Tyr Trp Gly Gly Thr Leu
            100                 105                 110

Val Thr Val Ser Ser
        115

<210> SEQ ID NO 25
<211> LENGTH: 117
<212> TYPE: PRT
<213> ORGANISM: Artificial Sequence
<220> FEATURE:
<223> OTHER INFORMATION: Heavy chain variable region of humanized BAT
      monoclonal antibody BATRHC

<400> SEQUENCE: 25

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115

<210> SEQ ID NO 26
<211> LENGTH: 117
<212> TYPE: PRT
<213> ORGANISM: Artificial Sequence
<220> FEATURE:
<223> OTHER INFORMATION: Heavy chain variable region of humanized BAT
      monoclonal antibody BATRHD

<400> SEQUENCE: 26

Gln Ile Gln Leu Val Gln Ser Gly Ser Glu Leu Lys Lys Pro Gly Ala
1               5                   10                  15
```

```
Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
            115

<210> SEQ ID NO 27
<211> LENGTH: 117
<212> TYPE: PRT
<213> ORGANISM: Artificial Sequence
<220> FEATURE:
<223> OTHER INFORMATION: Heavy chain variable region of humanized BAT
      monoclonal antibody BATRHE

<400> SEQUENCE: 27

Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Ala Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
            115

<210> SEQ ID NO 28
<211> LENGTH: 412
<212> TYPE: DNA
<213> ORGANISM: Artificial Sequence
<220> FEATURE:
<223> OTHER INFORMATION: Light chain variable region of humanized BAT
      monoclonal antibody BATRKd

<400> SEQUENCE: 28
aagcttgccg ccaccatgga catgagggtc cccgctcagc tcctggggct cctgctgctc      60
tggctcccag gtgccaaatg tgaaattgtg ttgacgcagt ctccatcctc cctgtctgca     120
tctgtaggag acagagtcac catcacttgc agtgccaggt caagtgtaag ttacatgcac     180
tggttccagc agaaaccagg gaaagcccct aagctctgga tctataggac atccaacctg     240
gcttctgggg tccatctag attcagcggc agtggatctg ggacatctta ctgtctcacc     300
atcaacagcc tgcagcctga agattttgca acttactatt gccagcaaag gagtagtttc     360
```

```
ccactcacgt tcggcggagg gaccaagctg gagatcaaac gtgagtggat cc        412
```

<210> SEQ ID NO 29
<211> LENGTH: 436
<212> TYPE: DNA
<213> ORGANISM: Artificial Sequence
<220> FEATURE:
<223> OTHER INFORMATION: Heavy chain variable region of humanized BAT
      monoclonal antibody BATRHC

<400> SEQUENCE: 29

```
aagcttgccg ccaccatgga ctggacctgg aggatcctct tcttggtggc agcagcaaca    60 ggtgccccact cccaggtgca gctggtgcaa tctgggtctg agcttaagaa gcctggggcc   120
tcagtgaaga tctcctgcaa ggcttctgga tatactttca caaactatgg aatgaactgg   180
gtgcgacagg cccctggaca agggcttcag tggatgggat ggataaacac cgacagtgga   240
gagtcaacat atgctgaaga gttcaaggga cggtttgtct tctccttgga cacctctgtc   300
agcacggcat atctgcagat caccagcctc acggctgagg acactggcat gtatttctgt   360
gcgaaagtcg gctacgatgc tttggactac tggggccagg gaaccctggt caccgtctcc   420
tcaggtgagt ggatcc                                                    436
```